(12) United States Patent
Cornell et al.

(10) Patent No.: US 11,141,374 B2
(45) Date of Patent: *Oct. 12, 2021

(54) NATURAL SKIN CARE COMPOSITIONS AND METHODS FOR TREATING OXIDATIVE STRESS AND RESTORING SKIN HEALTH

(71) Applicant: CODEX BEAUTY CORPORATION, Portola Valley, CA (US)

(72) Inventors: Marc Cornell, Cork (IE); Barbara A. Paldus, Portola Valley, CA (US); Jorge Iván Sanhueza Sepúlveda, Santiago (CL)

(73) Assignee: CODEX BEAUTY CORPORATION, Portola Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/189,553

(22) Filed: Mar. 2, 2021

(65) Prior Publication Data
US 2021/0177733 A1 Jun. 17, 2021

Related U.S. Application Data

(63) Continuation-in-part of application No. 17/166,503, filed on Feb. 3, 2021, which is a continuation-in-part of application No. 16/901,875, filed on Jun. 15, 2020.

(60) Provisional application No. 62/861,739, filed on Jun. 14, 2019.

(51) Int. Cl.
| | |
|---|---|
| *A61K 36/00* | (2006.01) |
| *A61K 8/9789* | (2017.01) |
| *A61Q 19/08* | (2006.01) |
| *A61Q 19/00* | (2006.01) |
| *A61Q 17/00* | (2006.01) |
| *A61K 8/99* | (2017.01) |
| *A61K 8/368* | (2006.01) |
| *A61K 8/34* | (2006.01) |
| *A61K 8/9794* | (2017.01) |

(52) U.S. Cl.
CPC ............ *A61K 8/9789* (2017.08); *A61K 8/345* (2013.01); *A61K 8/368* (2013.01); *A61K 8/9794* (2017.08); *A61K 8/99* (2013.01); *A61Q 17/00* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 4,933,177 A | 6/1990 | Grollier et al. | |
| 7,678,768 B2 | 3/2010 | Purpura et al. | |
| 10,300,012 B2 | 5/2019 | Gatto | |
| 10,721,937 B1 | 7/2020 | Cornell et al. | |
| 2006/0013839 A1* | 1/2006 | Yu | A61Q 1/06 424/401 |
| 2009/0028969 A1* | 1/2009 | Sene | A61K 8/602 424/757 |
| 2014/0017344 A1 | 1/2014 | Letelier Munoz et al. | |
| 2014/0128333 A1 | 5/2014 | Hancke Orozco et al. | |

FOREIGN PATENT DOCUMENTS

| | | |
|---|---|---|
| EP | 3398607 A1 | 11/2018 |
| GB | 2485483 A | 5/2012 |
| WO | 2006032091 A2 | 3/2006 |
| WO | 2013149323 A1 | 10/2013 |
| WO | 2014085946 A1 | 6/2014 |
| WO | 2019002714 A1 | 1/2019 |

OTHER PUBLICATIONS

Avello et al, Antioxidants and antimicrobial extracts of Aristotelia chilensis and Ugni molinae and its applications as preservatives in cosmetic products. Boletin Latinoamericano y del Caribe de Plantas Medicinales y Aromaticas (2009), vol. 8, No. 6, pp. 479-486 (Year: 2009).*
Backhouse et al., "Antinociceptive Activity of *Buddleja globosa* (Matico) in Several Models of Pain," Journal of Ethnopharmacology, vol. 119, Jun. 28, 2008, pp. 160-165.
Suwalsky et al., "Human Erythrocytes are Affected In Vitro by Flavonoids of *Aristotelia chilensis* (Maqui) Leaves," International Journal of Pharmaceutics, vol. 363, Jul. 16, 2008, pp. 85-90.
Arancibia-Avila et al., "Partial Characterization of a New Kind of Chilean Murtilla-like Berries," Food Research International, vol. 44, Jan. 5, 2011, pp. 2054-2062.
Vidal et al., "Microencapsulation of Maqui (*Aristotelia chilensis* [Molina] Stuntz) Leaf Extracts to Preserve and Control Antioxidant Properties," Chilean Journal of Agricultural Research, vol. 73, Issue 1, Mar. 31, 2013, 8 Pages.
Avello et al., "Antioxidant and Antimicrobial Extracts of Aristotelia Chilensis and Ugni Molinae and their Applications as Preservatives in Cosmetic Products," Latin American and Caribbean Bulletin of Medicinal and Aromatic Plants, vol. 8, No. 6, Nov. 30, 2009, 14 Pages.

(Continued)

*Primary Examiner* — Qiuwen Mi
(74) *Attorney, Agent, or Firm* — Medler Ferro Woodhouse & Mills

(57) ABSTRACT

The present disclosure is directed to a composition intended for application onto human skin suffering from oxidative stress, the composition comprising: (1) a mixture of at least: (a) a leaf extract of *Aristotelia chilensis*; (b) a leaf extract of *Buddleja globosa*; (c) a leaf extract of *Ugni molinae*; (d) optionally, a bark/seed extract of *Entada phaseoloides*; (e) optionally, a blend of *Pfaffia paniculata, Ptychopetalum olacoides*, and *Lilium candidum* extracts; and (f) at least one humectant; (2) an emulsifier; (3) a dermatologically acceptable carrier; and (4) a film former, wherein (a)-(f) are employed in amounts sufficient to neutralize existing free radicals present in the skin, while proactively priming the skin in order to enhance its ability to protect itself against free radical aggression caused by exposome-induced oxidative stress and dry skin-inducing water loss, wherein the composition is natural and free of a skin sensitizing-effective amount of an essential oil.

20 Claims, 10 Drawing Sheets

(56) References Cited

OTHER PUBLICATIONS

International Search Report and Written Opinion from PCT Application No. PCT/US2020/037756, dated Sep. 10, 2020.
Bradford, "A Rapid and Sensitive Method for the Quantitation of Microgram Quantities of Protein Utilizing the Principle of Protein-Dye Binding," Analytical Biochemistry, vol. 72, Jan. 29, 1976, pp. 248-254.
Backhouse et al., "Analgesic, Anti-Inflammatory and Antioxidant Properties of *Buddleja globosa*, Buddlejaceae," Journal of Ethnopharmacology, vol. 116, Nov. 22, 2007, pp. 263-269.
Dawane et al., "Experimental Evaluation of Anti-Inflammatory Effect of Topical Application of Entada Phaseoloides Seeds as Paste and Ointment," North American Journal of Medical Sciences, Nov. 31, 2011, pp. 513-517.
Lim et al., "NADPH Oxidase is a Novel Target of Delphinidin for the Inhibition of UVB-Induced MMP-1 Expression in Human Dermal Fibroblasts," Experimental Dermatology, vol. 22, Apr. 18, 2013, pp. 417-437.
Puri et al., "Effects of Air Pollution on the Skin: A Review," Indian Journal of Dermatology, Venereology, and Leprology, vol. 83, Issue 4, Jul.-Aug. 2017, pp. 415-423.
Lopez et al., "Murta (*Ugni molinae* Turcz) A Review on Chemical Composition, Functional Components and Biological Activities of Leaves and Fruits," Chilean Journal of Agricultural and Animal Sciences, vol. 34, No. 1, Oct. 31, 2017, pp. 43-56.
Araviiskaia et al., "The Impact of Airborne Pollution on Skin," Journal of the European Academy of Dermatology and Venereology, vol. 33, Aug. 31, 2019, pp. 1496-1505.
Parrado et al., "Environmental Stressors on Skin Aging. Mechanistic Insights," Frontiers in Pharmacology, vol. 10, Article 759, Jul. 9, 2019, pp. 1-17.
Ryu et al., "Particulate Matter Induces Inflammatory Cytokine Production via Activation of NFkB by TLR5-NOX4-ROS Signaling in Human Skin Keratinocyte and Mouse Skin," Redox Biology, vol. 21, Dec. 15, 2018, 16 Pages.
Liao et al., "The Impact of Particulate Matter (PM2.5) on Skin Barrier Revealed by Transcriptome Analysis: Focusing on Cholesterol Metabolism," Toxicology Reports, vol. 7, Nov. 25, 2019, pp. 1-9.
Schikowski et al., "Air Pollution and Skin Aging," Current Environmental Health Reports, vol. 7, Jan. 11, 2020, pp. 58-64.
Non-final Office Action in U.S. Appl. No. 17/166,503, dated May 27, 2021.

\* cited by examiner

NATURAL SKIN CARE COMPOSITIONS AND METHODS FOR TREATING OXIDATIVE STRESS AND RESTORING SKIN HEALTH

This is a continuation-in-part application of application Ser. No. 17/166,503, filed Feb. 3, 2021, which is a continuation-in-part of application Ser. No. 16/901,875, filed Jun. 15, 2020, which claims priority to U.S. Provisional Application No. 62/861,739, filed Jun. 14, 2019, the entire contents of both being hereby incorporated in their entirety by reference.

FIELD OF THE INVENTION

The present disclosure generally relates to compositions and methods for treating skin suffering from oxidative stress, as well as inhibiting oxidative stress from occurring. More particularly, the disclosure is directed to the use of specific associations of botanical extracts, film formers, and preservative systems to arrive at compositions and methods of enhancing the antioxidant defense potential, hydration, and barrier effect of skin suffering from oxidative stress, as well as inhibiting airborne pollutant-induced oxidative stress from occurring.

BACKGROUND

Skin is subject to damage by a number of extrinsic (environmental) and intrinsic factors. Examples of extrinsic factors include exposure to ultraviolet (UV) rays emanating from the sun, high energy visible light (violet-blue) emitted by devices such as TV/computer/smartphone screens, as well as harmful chemical agents found in airborne pollution such as smog and cigarette smoke. See, for example, Puri P, Nandar S K, Kathuria S, Ramesh V. "Effects o air pollution on the skin: A review." Indian J Dermatol Venereol Leprol. 2017 July-August; 83(4):415-423. doi: 10.4103/0378-6323, 199579. PMID: 28195077; Schikowski T, Hüls A. "*Air Pollution and Skin Aging.*" Curr. Environ. Health Rep. 2020 March; 7(1):58-64. doi: 10.1007/s40572-020-00262-9. PMID: 31927691; and Araviiskaia E, Berardesca E. Bieber T. et al. "*The impact of airborne pollution on skin.*" J. Eur. Acad. Dermatol Venereol. 2019; 33(8):1496-4505. doi: 10.1111./jdv.15583. Intrinsic factors that negatively impact skin include, for example, chronological aging, a person's genetic makeup, and other biological changes that occur from within the skin. These factors cause the skin to experience deleterious cellular effects associated with oxidative stress caused by harmful free radicals in the skin. Some of the most common free radicals are included within a group of reactive compounds termed reactive oxygen species (ROS). The three primary species of ROS include the superoxide anion ($O_2.^-$), hydrogen peroxide ($H_2O_2$), and the hydroxide radical (HO.).

$O2.-$ and HO. are commonly referred to as "free radicals." They can react with organic substrates and lead to intermediate species able to produce other ROS further. For instance, H atom abstraction by HO. free radicals on a C—H bond leads to a carbon-centered radical that further rapidly reacts with O2 to give a peroxyl radical RO2.. The latter may react with another substrate to give a new carbon-centered radical and a hydroperoxide ROOH, which may decompose into an alkoxyl radical RO in a reaction catalyzed by redox competent metal cations such as iron or copper (e.g., as occurring with heme proteins). These "secondary" species are all ROS and share a similarity in structure and reactivity with the three primary species $O_2.^-$, $H_2O_2$, and HO..

Many individuals purposefully expose their skin to harmful UV radiation by sunbathing or using tanning beds in an effort to obtain a suntan, considered by many to be a sign of beauty and affluence. Unfortunately, although the immediate effects of ultraviolet radiation may be considered aesthetically and socially gratifying, the long-term hazards, including the risk of oxidative stress, are cumulative and potentially quite serious, as is evidenced by the size of the global sunscreen market. This market has grown considerably in recent years, with many new products being introduced each and every year. What used to be considered a seasonal business is now viewed as one requiring year-round attention. Sun protection actives, meant to absorb and/or reflect harmful UV rays, are now included in a wide variety of personal products, particularly cosmetic products meant to be worn daily. For example, many cosmetics include compounds that prevent or combat the premature aging of skin; a phenomenon termed photoaging.

As explained herein, free radicals steal electrons from healthy cells in the skin, causing oxidative stress. This in turn activates enzymes in the skin that break down collagen and damage the DNA of a cell, resulting in sunburn and premature aging. Photoaging is characterized by wrinkling and yellowing of the skin, along with other physical changes such as cracking, telangiectasia (spider vessels), solar keratosis (growths), ecchymoses (subcutaneous hemorrhagic lesions), and loss of elasticity (sagging). It results from repeated exposure to UV light. Usually, the primary short-term hazard of prolonged exposure to UV light is erythema, i.e., sunburn. UV rays with wavelengths in the 290-320 nm range, designed as UVB rays, tend to be the primary cause of erythema. While UVA rays (320-400 nm) are also known to cause erythema, UVB rays are known to play a significant role in photoaging due to their ability to penetrate more deeply into the skin and cause free-radical formation throughout the epidermal and dermal layers.

Exposure to UV radiation is known to cause direct DNA damage within skin cells and can additionally lead to forms of indirect DNA damage through ROS generation. In addition to causing DNA damage, ROS generated by UV exposure can damage other components of the cell (e.g., proteins, lipids, and organelles). Sufficient DNA damage or even an excess in the cellular levels of ROS can initiate apoptosis, a form of programmed cell death, and/or an inflammatory response. ROS and other free radicals are generated during inflammation and can further impact the health and homeostasis of the skin. For example, during this cascade of events, enzymes are activated in the skin to break down collagen. Taken together, the direct DNA damage and ROS generation caused by UV exposure contribute to photoaging.

Regarding other environmental aging factors such as air pollution like smog and cigarette smoke, chemicals present therein are either themselves free radicals such as, for example, nitrogen dioxide ($.NO_2$), or have the ability to drive free-radical formation. These free radicals, when present within a biological setting such as the skin, react with organic and inorganic compounds, often perverting their structure/function in a deleterious way. The importance of this process lies in the reactivity of the molecules involved.

Under normal conditions, electrons orbit around atomic nuclei within distinct spatial orbitals that are arranged within groups of hierarchically ordered electron shells. The number and type of orbitals increase with increasing atomic number, filling in various electron shells. In general, a "full" orbital consists of a pair of electrons having opposite spins and results in a stable or non-reactive orbital. When an atom has an orbital that is partially filled, particularly in the valence shell, the single unpaired electron encourages chemical reactivity. This is common to many elements and is the impetus for the formation of larger compounds from discrete elements. However, in the case of free radicals like ROS, the additional electron creates a reactive inorganic compound that is potentially dangerous because it can react indiscriminately with neighboring molecules such as proteins, DNA, and vital cellular structures such as the cell membrane or other organelles.

High cellular concentrations of free radicals can cause extensive cellular damage. The extent of damage depends on the availability of cellular defense mechanisms such as antioxidants or specialized enzymes that are designed to neutralize free radical reactivity (e.g., superoxide dismutase and peroxidases).

These cellular defense mechanisms help reduce the amount of damage free radicals and other reactive species may cause to the skin by scavenging free radicals or enzymatically converting the free radicals to a less toxic compound. The body's antioxidant defense system can become impaired, however, by the aging process and/or compromised by, for example, inflammation/erythema, infection, genetic predisposition, or and other disorders affecting the generation of or response to oxidative stress.

Oxidative stress has also been found to negatively impact water homeostasis of the skin, i.e., the ability of the skin to maintain consistent hydration levels. It is important to the health and appearance of skin to keep it properly hydrated and nourished, counteracting the damage caused by oxidative stress. Dry skin is a particularly common disorder that affects both males and females equally and is particularly prevalent in older individuals and those genetically predisposed to such a condition. People suffering from dry skin complain of flaking, itching, irritation, and an overall dull, rough, and lackluster appearance to their skin.

Moreover, as a person ages, their skin tends to produce fewer natural oils that aid in preventing moisture from escaping from and thus dehydrating the skin. Disruption of water homeostasis occurs at an early stage as a person's skin ages. This is, in part, because the expression of aquaporin-3, one of the proteins that regulate water flow at a cellular level, decreases as a person ages. Skin lacking proper hydration cannot communicate nutrients throughout the organ for proper cellular maintenance. Further, hydration status regulates sodium flux and inflammatory pathways in the skin, and when dehydrated, the skin becomes irritated and inflamed. Thus, by maintaining good hydration of the epidermis, particularly the outermost layer of epidermal cells called the stratum corneum (a.k.a. the horny layer) inflammation is reduced and less ROS is generated thereby. This enhances the effectiveness of endogenous antioxidant molecules, as well as cosmetic agents exhibiting antioxidant properties, to help alleviate or respond to oxidative stresses and free radical formation. In particular, properly hydrated skin slows photoaging by helping to maintain skin elasticity.

As alluded to above, the skin has a strong innate antioxidant defense to protect against UV-induced oxidative stress and free radical formation. This is accomplished via a cadre of endogenous antioxidant enzymes, such as superoxide dismutase (SOD), peroxidase, and catalase, along with endogenous antioxidant compounds. Glutathione (GSH) is an exemplary cellular antioxidant that serves—in its reduced state—as the substrate for enzymatic neutralization of hydrogen peroxide to water. The resultant oxidized glutathione can be recycled back to its reduced form by an NADPH-dependent reductase, thereby allowing it to once again serve as an antioxidant. Unfortunately, excessive exposure to UV radiation can overwhelm the cutaneous antioxidant capacity, leading to oxidative damage and ultimately to immunosuppression and/or serious skin disorders such as photoaging and skin cancer.

The skin's barrier function is another important defense against oxidative stress. The term "barrier function" refers to the functions predominantly provided by the outermost layer of the skin, the stratum corneum, a.k.a. "the horny layer" or "the skin barrier," which is responsible for retaining moisture within the lower layers of epidermal cells and for keeping damaging elements like UV rays, pollutants, and pathogens out. When the skin's barrier function is operating properly, skin is firm, plump, and hydrated. However, when the barrier function deteriorates or is compromised, skin health deteriorates as well.

The stratum corneum is the primary line of defense between an individual and the outside world, preventing environmental chemicals and biological irritants from penetrating the skin. For example, microbes, allergens, toxic chemicals, UV light, and the like are blocked by the stratum corneum from penetrating the skin. This is referred to as the stratum corneum's "physical" defense mechanism.

While protection against external assaults is a very important function served by the stratum corneum, a similarly important function is to prevent the escape of water. The stratum corneum is made up of multiple stacks of flattened cells or corneocytes, each encased in a thick coating of fat, a.k.a., lipids. If one were to compare the stratum corneum to a brick wall, the stack of cells are bricks, and the fatty matrix encasing them is the mortar. Together, they form a barrier that keeps skin's water content inside so that the skin stays firm, hydrated, elastic, and less prone to wrinkling.

The lipid portion of the stratum corneum is primarily responsible for the water-sealing properties. These lipids are comprised of various oily compounds naturally produced by the human body, including diglycerides, triglycerides, fatty acids, ceramides, cholesterol, and squalene. These lipids form a semi-permeable, waterproofing multi-layered matrix that surrounds the skin cells and provides structure to the skin barrier by holding the skin cells tightly in place.

One of the ways by which the stratum corneum is often damaged involves an individual's personal skin care routine. For example, daily cleansing of the skin with cleansers having an overly alkaline pH (skin naturally has a slightly acidic pH) or containing aggressive surfactants such as sulfates, over time, wears away the corneocytes and lipid matrix of the stratum corneum resulting in cracks and gaps being formed therein. This same deleterious phenomenon is observed when using anti-aging products. Many serums and cosmetic creams contain high concentrations of aggressive active ingredients meant to stimulate cell turnover and reduce the appearance of fine lines and wrinkles. Examples of such ingredients include retinols, ascorbic acid (Vitamin C), and alpha hydroxy acids such as glycolic acid. Routine application of these products leads to stratum corneum damage and loss of hydration barrier function as the high potency actives wear out the integrity of the stratum corneum's skin cells and lipids.

The stratum corneum can also be damaged by various extrinsic (environmental) and intrinsic factors. Examples of extrinsic factors include exposure to the aforementioned UV rays, high energy visible light (violet-blue light) emanating from TVs, computer screens, and smart phones, as well as harmful chemical agents found in airborne pollutants like car exhaust, smog, and cigarette smoke. Intrinsic factors that can negatively impact the stratum corneum include, for example, chronological aging, a person's genetic makeup, and other biological changes that occur within the skin and body. These factors have deleterious cellular effects on the stratum corneum due to oxidative stress caused by harmful free radicals.

More particularly, while the damage caused by UV rays in terms of sunburn, photoaging, and skin cancer have been extensively studied, UVB rays have also been found to cause damage to the stratum corneum upon exposure. This is believed to be caused by delamination of the stratum corneum's lipid matrix resulting in a decrease in intercellular strength, strain, and cohesion between the corneocytes and lipids. UV exposure also naturally dries out the skin. Once the skin becomes dry and flaky, the ability of the corneocytes and lipids to form a strong, cohesive matrix is compromised, leading to cracks and gaps being formed within the stratum corneum and thereby providing a pathway for pathogens to enter and water to escape.

The negative impact of ROS and other free radicals on the stratum corneum is also highly problematic, as previously discussed. In addition to UV-induced free radicals, air pollutants like car exhaust, smog, and cigarette smoke contain chemicals that are either themselves free radicals or can drive free-radical formation. These free radicals, when present within a biological setting such as the stratum corneum, cause damage to the lipids and proteins constituting the structural components of the stratum corneum. The extent of damage depends on the availability of neutralizing antioxidant cellular defenses produced by the body.

As was mentioned previously, because oxidative stress negatively impacts the ability of the skin to maintain constant hydration levels, it is important to the health and appearance of skin to keep it properly hydrated. Aside from drinking plenty of water, maintaining proper hydration levels is highly dependent on a properly functioning stratum corneum. A compromised stratum corneum, unable to effectively seal water within the skin, causes skin to become dry. People suffering from dry skin complain of flaking, itching, irritation, and an overall dull, rough, and lackluster appearance to their skin. Hence, while protection against external assaults is an important function served by the stratum corneum, an equally important function is to prevent dry skin-inducing water loss.

Despite its importance, the barrier formed by the stratum corneum is quite delicate and prone to thinning as a person ages. Moreover, any assault on the stratum corneum, either from external assaults or internal deficiencies, can lead to sensitized, dehydrated skin that is susceptible to environmental harm, dryness, irritation, breakout, sagging, and other signs of aging. When skin is dry, it is more permeable to irritants and allergens that can trigger inflammation. Beyond the free radical production and consequent damage attendant to inflammatory responses in the skin, the penetrating irritants and allergens can cause rosacea, acne, eczema, and premature aging.

The stratum corneum is under continuous assault by various extrinsic (environmental) factors. These include the aforementioned UV rays, high-energy visible light (violet-blue light), and harmful chemical agents found in airborne particulate matter pollutants like car exhaust, smog, and cigarette smoke. These factors have deleterious cellular effects on the stratum corneum due to oxidative stress caused by harmful free radicals and/or ROS.

The negative impact of free radicals/ROS on the stratum corneum is highly problematic. In addition to UV-induced free radicals, air pollution containing airborne particulate matter present in car exhaust, smog, and cigarette smoke contain chemicals that are either themselves free radicals or can drive free-radical formation. These free radicals, when present within a biological setting such as the stratum corneum, cause a flow of electrons from one molecule to another resulting in cellular damage and degradation of the stratum corneum in the process. The extent of damage depends on the availability of neutralizing antioxidant cellular defenses produced by the body. Unfortunately, the body is often incapable of naturally generating sufficient quantities of these antioxidant cellular defenses.

In view of the above, it is clear that in order to both effectively treat skin already damaged from oxidative stress and to protect against further damage by oxidative stress, at least three issues should be addressed. First, skin-resident free radicals should be neutralized to terminate ongoing damage from oxidative stress. Second, the skin should be rehydrated to restore osmotic balance, including replacement of any water/moisture lost. Lastly, the skin's barrier function should be repaired and/or restored to help protect the skin against further attack (e.g., by free radicals) stemming from both extrinsic and intrinsic factors as well as to prevent dry skin-inducing water loss.

Accordingly, there is a need for skin care compositions and methods that treat or address oxidative stress and restore skin health by neutralizing free radicals in the skin, rehydrating the skin, and repairing and/or protecting the skin's barrier function.

In addition to the above-noted physical defense mechanism of the stratum corneum, the skin also possesses a "biological" defense mechanism commonly referred to as its acid mantle. The acid mantle is a thin film formed on the surface of the stratum corneum and comprised of a mixture of oils produced by the body and amino acids present in sweat. The acid mantle's primary role is to maintain a healthy and diverse microbiome on the skin's surface. This diversity of bacteria, fungi, and viruses that comprise a healthy skin microbiome help to select against the colonization of potentially harmful pathogens and can drastically affect the potency and scent of body odor, among other things. Maintaining a healthy and diverse skin microbiome is also important for maximizing overall skin health and its ability to act as a biological defense mechanism for the host.

A corollary theory to the function of the acid mantle relates to its role in skin homeostasis, i.e., the interaction between cells, tissues, and organisms in the balanced maintenance and regulation of skin's biological functions. As the name implies, the skin barrier's acid mantle is acidic in nature, with a pH of from about 4.5 (more typical of males) to about 5.5 (more typical for females). The acidic nature of the acid mantle is one pressure on bacterial selection and, in turn, skin homeostasis which are important elements of proper skin barrier functionality.

Accordingly, there is also a need for skin care compositions and methods that address oxidative stress, rehydrate the skin, and repair and/or protect the skin's barrier function without unduly impairing the stratum corneum's acid mantle.

The totality of extrinsic factors an individual's skin is exposed to over the course of their lifetime is referred to as the "exposome." Studies have found that, over time, exposure to the exposome contributes to premature skin aging. See, Parrado C, Mercado-Saenz S, Perez-Davo A, Gilaberte Y, Gonzalez S, Juarranz A. *"Environmental Stressors on Skin Aging. Mechanistic Insights"*, *Front Pharmacol.* 2019; 10:759. Published 2019 Jul. 9. doi:10.3389/fphar.2019.00759.

When it comes to the UV light portion of the exposome, avoidance of UV-related oxidative stress is typically addressed by sunscreen-containing products having a sun protection factor (SPF) of at least 30. However, there is a dearth of products available on the market that address the common issue of oxidative stress caused by harmful particulate matter present in airborne pollution. Thus, the ability to effectively inhibit and treat oxidative stress caused by airborne pollutants is highly desirable.

Particulate matter is an airborne pollutant comprising a mixture of solid particles and liquid droplets that contain hundreds of different chemicals, including harmful chemicals such as sulfur dioxide, nitrogen oxides, heavy metals, and carbon monoxide. Particulate matter may range from dust, dirt, soot, or smoke to small droplets of liquid, dry solid fragments, and solid cores with liquid coatings. There are both anthropogenic and naturally occurring sources of particulate matter, including automobiles, power plants, factories, fires, wood-burning stoves, dust from open land, pollen, and cigarette smoke. Particulate matter, or "PM," vary in size from 10 microns or less ($PM_{10}$, typically referred to as "dust") to 2.5 microns or less ($PM_{2.5}$, typically referred to as "fine dust").

Due to their size, these particulates can float in the air indefinitely. They typically enter the body through the nose, mouth, and skin. Recent studies have shown that once these particulates contact the skin's stratum corneum/skin barrier, the toxic chemicals contained therein begin to trigger cell deformation and free radical formation, resulting in damage to the stratum corneum/skin barrier. See, for example, Zhengzheng Liao, Jing Nie, Peiwen Sun, "*The impact of particulate matter (PM2.5) on skin barrier revealed by transcriptome analysis: Focusing on cholesterol metabolism,*" Toxicology Reports, Volume 7, 2020, Pages 1-9, ISSN 2214-7500.

Airborne pollutants in particulate form are a significant cause of various skin issues and can exacerbate existing issues such as atopic dermatitis and acne. Once these pollutants attach themselves to skin, the resultant free radicals trigger secretion of inflammatory cytokines and an increase in leukocytes by the skin's cells resulting in an allergic reaction. For example, studies have shown that a person suffering from atopic dermatitis will experience a worsening of their condition on days in which the concentration of particulate matter present in the air is high, whereas their symptoms are alleviated on days of lower particulate matter concentration. See also, Ryu Y S, Kang K A, Piao M J, et al. "*Particulate matter induces inflammatory cytokine production via activation of NFκB by TLR5-NOX4-ROS signaling in human skin keratinocyte and mouse skin.*" Redox Biol. 2019; 21:101080. doi:10.1016/j.redox.2018.101080

Particulate matter has also been found to exacerbate skin dryness and itchiness. This happens because the oxidative stress caused by the exposure to particulate matter weakens the skin, thereby impeding its waste-removal and sebum-control functions. As a result, skin becomes dry and itchy and experiences premature aging that physically manifests in the form of age spots, wrinkles, scales, and the like.

Accordingly, there is a need for skin care compositions and methods that not only inhibit oxidative stress-inducing particulate matter from contacting the skin, but also neutralize free radicals and/or ROS associated with the particulate matter.

There is no shortage of conventional cosmetic products in the market meant to enhance the health and appearance of skin by combatting the negative effects associated with the influence of both extrinsic and intrinsic factors. However, the cosmetic industry has recently embraced a sub-category of these products deemed to be organic/natural, and there is a current trend by consumers towards these types of goods. These products are believed to possess health and environmental benefits. In line with the philosophy of such products, consumers also expect them to be paraben-free, phthalate-free, sulfate-free, silicone-free, synthetic fragrance-free, alcohol-free, phenoxyethanol-free, or otherwise non-toxic. This category of organic/natural products has become one of the fastest growing in the global personal care and cosmetic segments.

In response to the outstanding need in the industry for products that meet certain thresholds of "natural" and "organic" ingredients, coupled with the lack of official standards for what qualifies as "natural" and "organic," preservative formulation has become a cottage industry with consumers gravitating towards products containing natural extracts, botanicals, or other ingredients derived from natural sources, while avoiding those products having ingredients that are either known to cause or suspected of causing adverse health reactions. Unfortunately, this ad hoc approach and decentralization of acquired knowledge and experience of generating effective preservative formulations have led to a host of ineffective solutions that typically result in diminished shelf-life and usability of associated cosmetic consumer products.

Various third-party certifications have been established in an attempt to bring consistency and reliability to the use of natural and organic preservatives in topical consumer products. For example, ECOCERT® is an organic certification organization based in Europe that conducts inspections in over 80 countries, making it one of the largest organic certification organizations in the world. ECOCERT® primarily certifies food and food products but also certifies cosmetics, detergents, perfumes, and textiles, and is a leading certifier of fair-trade food, cosmetics, and textiles.

Another example is the Cosmetic Organic Standard (COSMOS), a Europe-wide private standard that was developed by five charter members: BDIH (Germany), Cosmebio (France), Ecocert Greenlife SAS (France), ICEA (Italy), and Soil Association (Great Britain). They were all combined under an AISBL (international non-profit organization based in Brussels), the purpose of which was to set out minimum common requirements, harmonize organic and natural cosmetic certification rules, and lobby institutions in the sector's interests. COSMOS makes use of the principles in the ECOCERT® standard: to promote the use of ingredients from organic farming, use production and manufacturing processes that are environmentally sound and safe for human health, and include and expand the concept of "green chemicals."

The National Organic Program (NOP), a federal regulatory framework in the United States governing organic food, is yet another certification. The core mission of the NOP is to protect the integrity of the United States Department of Agriculture (USDA) organic seal. The seal is used for products adhering to USDA standards that contain at least 95% organic ingredients.

Hence, the industry has increased its efforts to develop "natural" cosmetic formulations using non-synthetic ingredients. This approach differs from the synthetic ingredient-based approach that has allowed the cosmetic industry to develop cosmetics with consistent product integrity, performance, and shelf life through the use of harsh, irritating, synthetic ingredients such as phenoxyethanol.

Accordingly, there is also a need for skin care compositions and methods for treating or addressing oxidative stress and restoring skin health that are natural and free of harsh, irritating, synthetic ingredients while providing effective broad-spectrum preservative protection as well as promoting or cooperating with ingredients for treating and inhibiting exposome-induced oxidative stress.

The use of botanical extracts on skin, in general, is known. However, based on only the sheer number of botanical extract candidates in existence, together with extraction techniques and solvents that may be used, a virtually infinitesimal number of products can be formulated with no assurance that the composition made will be both stable and useful for its desired purpose. Consequently, the ability to formulate skin treatment products, in the absence of skin-sensitizing ingredients, that are natural, highly efficacious and stable, is a daunting challenge as the inventors have discovered. One cannot merely combine a mixture of random botanical extracts, in arbitrary concentrations, using arbitrary extraction techniques and solvents, with the expectation that all of the disparate ingredients contained therein will be both compatible to one another, and yield the intended benefits and properties.

For example, U.S. Pat. No. 4,933,177 discloses the use of certain botanical ingredients for application onto skin. However, the reference is devoid of any specific teaching or suggestion regarding the precise association of ingredients, extraction techniques and solvents to be used, as well as which types of ingredients are to be avoided, in order to formulate an efficacious, natural product capable of enhancing skin health and appearance.

Similarly, U.S. Pat. No. 7,678,768; GB 2485483; WO 2006/032091; WO 2012/033422; WO 2013/149323; and WO 2019/002714 all disclose botanical ingredients for application onto skin for a plethora of potential uses. However, not only do these references disclose a small sample size of puzzle-piece candidates available to a formulator, but when one also considers the amounts in which each of these ingredients may be used, together with all the other variables that must be taken into consideration when formulating with plant extracts, to say that successfully arriving at a targeted product is like finding the proverbial needle in a haystack, is indeed an understatement.

One of the major deterrents associated with the use of botanical ingredients in skin care compositions relates to their relative instability in products as evidenced by loss of potency, odor deviations, and discoloration. These negative attributes increase the risk of microbiological contamination and proliferation, instability, and inadequate safety of the products. This problem becomes even more acute when the composition has to qualify as being "natural." The elimination of conventionally used synthetic, inorganic, and/or petroleum-derived ingredients from a formulator's toolbox severely hampers their ability to make efficacious, yet stable, skin treatment products. One might argue that a formulator skilled in the art could determine, through routine experimentation, which botanical extracts, auxiliary ingredients, excipients, solvents, and amounts of each can be combined in order to arrive at an intended product. However, as was mentioned above, in view of the sheer number of combinatorial permutations that exist, based on the number of ingredients that may be chosen, causes the successful formulation of such a product to be based more on luck and happenstance, as opposed to routine experimentation.

Based on the foregoing, it is an object of embodiments of the present disclosure to provide natural, organic and ECOCERT®-approved skin care compositions and methods that are effective at treating and priming skin damaged by oxidative stress.

Another object of embodiments of the present disclosure is to provide natural, organic and ECOCERT®-approved compositions and methods capable of proactively priming the skin and enhancing its ability to defend against free-radical aggression.

Another object of embodiments of the present disclosure is to provide skin care compositions and methods having effective broad-spectrum anti-microbial activity using natural ingredients while treating or addressing oxidative stress and/or priming the skin against free-radical aggression.

Another object of embodiments of the present disclosure is to provide skin care compositions and methods that protect skin from exposome-induced oxidative stress without unduly impairing the stratum corneum's acid mantle/skin microbiome that are natural, free of harsh, irritating, and/or synthetic ingredients, and are capable of inhibiting oxidative stress-inducing particulate matter from contacting the skin while neutralizing free radicals/ROS associated with the particulate matter.

SUMMARY

The present disclosure is directed to a composition intended for application onto human skin, the composition that includes (1) a mixture of at least: (a) a leaf extract of *Aristotelia chilensis*; (b) a leaf extract of *Buddleja globosa*; (c) a leaf extract of *Ugni molinae*; and (d) optionally, a bark/seed extract of *Entada phaseoloides*; (e) optionally, a blend of *Pfaffia paniculata, Ptychopetalum olacoides*, and *Lilium candidum* extracts; and (f) at least one humectant; (2) an emulsifier; (3) a dermatologically acceptable carrier; and (4) a film former, wherein (a)-(f) are employed in amounts sufficient to synergistically neutralize existing free radicals present in the skin, while proactively priming the skin by repairing and/or protecting its stratum corneum without unduly impairing the stratum corneum's acid mantle, in order to enhance its ability to defend itself against free-radical aggression, exposome-induced oxidative stress, and dry skin-inducing water loss, thereby improving its health and appearance, and wherein the composition is natural, free of a skin-sensitizing amount of an essential oil, and has a pH ranging from about 4.5 to about 5.5, and preferably from about 4.8 to about 5.3.

According to another embodiment, the present disclosure is also directed to a composition intended for application onto human skin, the composition that includes (1) a preservative system; (2) a mixture of at least: (a) a leaf extract of *Aristotelia chilensis*; (b) a leaf extract of *Buddleja globosa*; and (c) a leaf extract of *Ugni molinae*; and (d) optionally, a bark/seed extract of *Entada phaseoloides*; (e) optionally, a blend of *Pfaffia paniculata, Ptychopetalum olacoides*, and *Lilium candidum* extracts; and (f) at least one humectant; (3) an emulsifier; (4) a dermatologically acceptable carrier; and (5) a film former, wherein (a)-(f) are employed in amounts sufficient to synergistically neutralize existing free radicals present in the skin, while proactively priming the skin by repairing and/or protecting its stratum corneum without unduly impairing the stratum corneum's acid mantle, in order to enhance the skin's ability to defend itself against free-radical aggression, exposome-induced oxidative stress, and dry skin-inducing water loss, thereby improving its health and appearance, and wherein the composition is natural, free of a skin-sensitizing amount of an essential oil, and has a pH ranging from about 4.5 to about 5.5, and preferably from about 4.8 to about 5.3.

The present disclosure is also directed to a method of treating and priming skin suffering from or at risk of suffering from oxidative stress in order to enhance its health and appearance by applying one of the above-disclosed compositions onto the skin.

According to another embodiment, the present disclosure is also directed to a method of proactively priming the skin by repairing and/or protecting its stratum corneum without unduly impairing the stratum corneum's acid mantle, in order to enhance the skin's ability to defend itself against free-radical aggression and dry skin-inducing water loss.

According to yet another embodiment, the present disclosure is also directed to a method of inhibiting oxidative stress-inducing particulate matter from contacting the skin and neutralizing free radicals/ROS associated with the particulate matter.

According to yet another embodiment, the present disclosure is directed to a natural preservative system that cooperates with a skin care composition and method for treating or addressing oxidative stress. The preservative system may be a preservative system as discussed and/or claimed in U.S. Pat. No. 10,721,937 which issued on Jul. 28, 2020 and which enjoys a priority date of May 9, 2019. This reference is incorporated herein by reference in its entirety.

According to yet another embodiment, the present disclosure is directed to a skin care composition intended for application to the skin as a sun block or sunscreen product.

These and other features, aspects and advantages of the present disclosure will become evident to those skilled in the art from a reading of the present disclosure.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1:
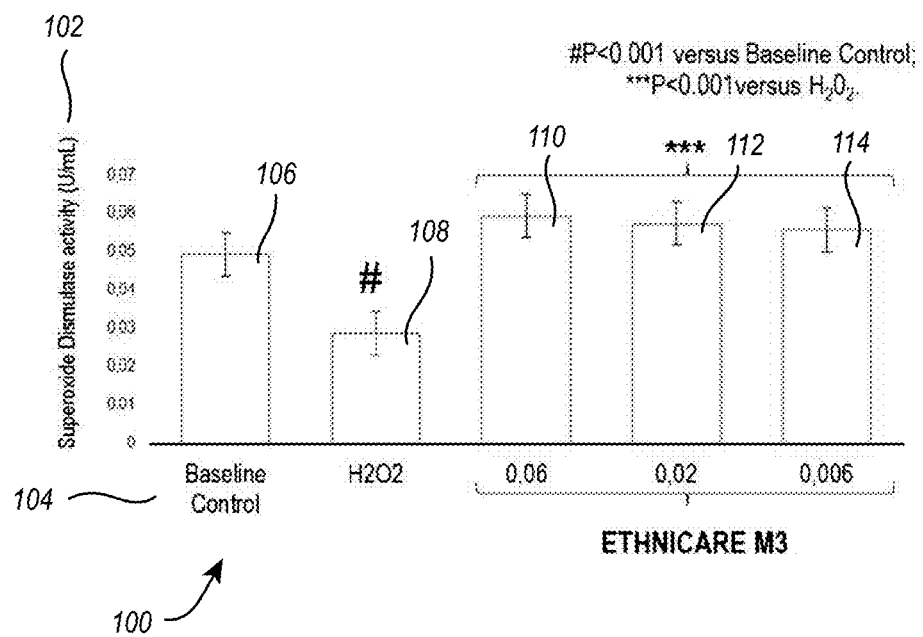
FIG. 1 illustrates levels of superoxide dismutase activity in response to different compositions including components of embodiments of the disclosure.

For purposes of the present disclosure, the use of the word "natural" is intended to encompass ECOCERT®-approved ingredients or formulations synonymous with the terms "green," "clean," "organic," "sustainable," "eco-friendly," or "environmentally-friendly" as known and used in the art. The term "natural," for example, may be used in the context of holistic or homeopathic formulations and is intended to include those topical consumer products and/or preservative systems that are plant-based, paraben-free, and/or non-toxic.

Further, when used in the context of the antimicrobial properties of a preservative or preservative system, the term "broad spectrum" is intended to describe those preservatives or preservative systems of the present disclosure that have the ability to inhibit the growth of or kill a wide range of microorganisms that decay or spoil topical consumer products. For example, a "broad spectrum" preservative system inhibits the growth of or kills a wide range of bacteria and fungi, preferably a wide range of Gram-positive and Gram-negative bacteria, yeasts, molds, and/or other fungi.

The compositions of the present disclosure can comprise, consist essentially of, or consist of, the components of the present disclosure as well as other ingredients described herein. The term "comprising" as used herein is meant to include various optional, compatible components that can be used in the preservative systems and cosmetic compositions of the present disclosure without limiting the inclusion, use of, or cooperation with other ingredients, excipients, uses, or otherwise. The term "consisting essentially of" as used herein means that the composition or component may include additional ingredients, but only if the additional ingredients do not materially alter the basic and novel characteristics of the compositions or methods.

As used herein, the words "preferred," "preferably," and variants thereof refer to embodiments of the disclosure that afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the disclosure.

Numerical ranges as used herein are intended to include every number and subset of numbers contained within that range, whether specifically disclosed or not. Further, these numerical ranges should be construed as providing support for a claim directed to any number or subset of numbers within that range.

All percentages, parts, proportions, and ratios as used herein are by weight of the total composition, unless otherwise specified. All such weights as they pertain to listed ingredients are based on the active level.

All references to singular characteristics or limitations of the present disclosure shall include the corresponding plural characteristic or limitation, and vice versa, unless otherwise specified or clearly implied to the contrary by the context in which the reference is made.

All publications, articles, papers, patents, patent publications, and other references cited herein are hereby incorporated in their entireties for all purposes to the extent consistent with the disclosure herein.

The terms "prime" and "priming" as described herein refer to the process of repairing and/or protecting the stratum corneum without unduly impairing its acid mantle in order to protect it from oxidative stress and dry skin-inducing water loss. One exemplary way that the acid mantle could be considered unduly impaired is by observing a reduced diversity or unnatural selection of microbes comprising the skin microbiome. This may correlate with a skin pH outside of normal homeostatic bounds. The terms "prime" and "priming" may further refer to the process of inhibiting oxidative stress-inducing particulate matter from contacting the skin and neutralizing free radicals/ROS associated with the particulate matter in order to proactively protect the stratum corneum from oxidative stress and dry skin-inducing water loss.

The term "dry skin-inducing water loss" as described herein refers to an amount of trans-epidermal water loss (TEWL) that causes skin to become dry, flaky, itchy and/or irritated—symptomatic of an improperly functioning stratum corneum/skin barrier.

The term "oxidative stress" as described herein refers to the disturbance in balance between reactive oxygen species (ROS) and/or free radicals and antioxidants present in the skin caused by extrinsic and/or intrinsic factors. Extrinsic factors include, for example, exposure to UV radiation, high energy visible light, pollution, and products containing harsh chemicals. Intrinsic factors include, for example, chronological aging, a person's genetic makeup, and other biological changes that occur from within the skin.

The term "skin-sensitizing effective amount" as described herein is meant to exclude an amount of a volatile essential oil that can lead to an allergic response following contact with an individual's skin. Skin sensitization is an immunological response to previous exposure to a substance that results in an inflammatory skin reaction. An allergic skin reaction is usually presented as a red, itchy, bumpy rash. Examples of the types of volatile essential oils that can cause skin sensitization, depending on their amounts within a skin care composition include, but are not limited to, frankincense, myrrh, and sweet orange.

The term "free radicals" as described herein refers to those ROS that are formed when skin experiences oxidative stress caused by extrinsic factors including exposure to UV radiation and environmental stressors such as pollution and harmful chemical agents typically found, for example, in hard-surface cleaning products.

The present disclosure generally relates to compositions and methods for effectively alleviating oxidative stress in order to enhance human skin's health and appearance, while at the same time or alternatively enabling the skin to defend itself against further free-radical aggression and dry skin-inducing water loss by repairing and/or protecting the stratum corneum/skin barrier in a way that does not unduly impair its acid mantle. Moreover, the composition is also natural, organic, and ECOCERT®-approved, thus being free of synthetic and/or petroleum-derived ingredients.

It has surprisingly been discovered by the inventors that a composition that is both natural and free of a skin sensitizing-effective amount of an essential oil, comprising: (1) a mixture of specific botanical infusions comprising at least: (a) a leaf extract of *Aristotelia chilensis*; (b) a leaf extract of *Buddleja globosa*; (c) a leaf extract of *Ugni molinae*; (d) optionally, a bark/seed extract of *Entada phaseoloides*; and (e) optionally, a blend of *Pfaffia paniculata, Ptychopetalum olacoides*, and *Lilium candidum* extracts; (2) at least one humectant; (3) an emulsifier; (4) a dermatologically acceptable carrier; and (5) a film former, when applied onto skin, synergistically alleviates oxidative stress in order to enhance the skin's health and appearance, while at the same time priming the skin by repairing and/or protecting the stratum corneum without unduly impairing its acid mantle, in order to enable the skin to protect itself against free radical aggression caused by exposome-induced oxidative stress and dry skin-inducing water loss.

Moreover, the inventors have also surprisingly and unexpectedly discovered that the composition of the present invention also inhibits oxidative stress-inducing particulate matter present in airborne pollutants from contacting the skin, while simultaneously neutralizing free radicals and/or ROS associated with and/or resulting from the particulate matter without unduly impairing the stratum corneum's acid mantle/skin microbiome

*Aristotelia chilensis* leaf extract is derived from the leaves of a small dioecious evergreen tree in the Elaeocarpaceae family native to South America in the Valdivian temperate rainforests of Chile, which also goes by the name maqui. The extract has been found to contain high amounts of anthocyanins, indole alkaloids, and flavonoids. These compounds serve as a source of antioxidants that help to neutralize free radicals and protect the skin's DNA.

This extract has also been found to be rich in the anthocyanidin delphinidin. In a study entitled "NADPH oxidase is a novel target of delphinidin for the inhibition of UVB-induced MMP-1 expression in human dermal fibroblasts," Lim T G, Jung S K, Kim Y, Lee H J, Jang T S, Lee K W, *John Wiley & Sons Ltd, Experimental Dermatology,* 2013, 22, 417-437, it was reported that delphinidin was effective at inhibiting UVB-induced MMP-1 expression in the skin, which is known to cause degradation of dermal collagen. Various enzyme systems in the skin are associated with endogenous ROS production, including the enzyme system NADPH oxidase (NOX), which plays a key role in triggering ROS production. Studies have shown that NOX activation is thus closely related to ROS-induced skin aging. The study concluded that delphinidin significantly inhibits UVB-induced MMP-1 expression in human dermal fibroblasts, which then inhibits NOX enzyme activation, which in turn inhibits ROS production, and therefore this particular anthocyanidin might prevent photoaging.

This extract is commercially available from N-Active EIRL under the trade name EthniCare® MAQUI.

The *Aristotelia chilensis* leaf extract is preferably employed in an amount of from about 1 to about 10% by weight, and most preferably from about 2 to about 5% by weight, based on the total weight of the composition.

*Buddleja globosa* leaf extract is derived from the leaves of the orange ball buddleja, a.k.a. matico, a species of flowering plant endemic to Chile and Argentina. The extract has been found to contain glycosidic flavonoids and phenylethanoids such as verbascoside, iridoids, triterpenoids, and di- and sesquiterpenoids, together with two caffeic acid derivatives. These compounds have shown promise in wound healing due to their ability to promote fibroblast growth, with a strong antioxidant effect. This particular leaf extract is also rich in stigmasterol, an unsaturated plant sterol found in plant oils.

In an article entitled "Analgesic, anti-inflammatory, and antioxidant properties of *Buddleja globosa*, Buddlejaceae," Backhouse N, Rosales L, Apablaza C, Golly L, Erazo S, Negrete R, Theodoluz C, Rodriguez J. Delporte C J, *Ethnopharmacol*. 2008 Mar. 5; 116(2):263-9, it was reported that plant extracts having fractions rich in stigmasterol and β-sitosterol display anti-inflammatory properties. This extract is commercially available from N-Active EIRL, under the trade name EthniCare® MATICO.

The *Buddleja globosa* leaf extract is preferably employed in an amount of from about 0.5 to about 3% by weight, and most preferably from about 1 to about 2% by weight, based on the total weight of the composition.

*Ugni molinae* leaf extract is derived from the leaves of a woody evergreen shrub from the myrtaceae family commonly found in Chile, and is also known by its Spanish name murta. The extract has been found to contain various phenolic compounds including gallic acid, catechin, quercetin, myricetin, and kaempferol. These compounds have been found to possess strong antioxidant activity against ROS production, lipid peroxidation, and superoxide anion production.

In an article entitled "MURTA (*Ugni molinae* Turcz.): A REVIEW ON CHEMICAL COMPOSITION, FUNCTIONAL COMPONENTS AND BIOLOGICAL ACTIVITIES OF LEAVES AND FRUITS," Lopez J, Vega-Galvez A, Rodriguez A, Uribe E, Bilbao-Sainz C, Chilean *J. Agric. Anim. Sci., ex Agro-Ciencia* (2018) 34(1):1-14, the *Ugni molinae* leaf extract was found to have large amounts of flavonoids (anthocyanins, flavonols, flavanols), condensed and hydrolyzable tannins, stilbenoids (resveratrol), and phenolic acids, which possess both antioxidant and antimicrobial activity. As was mentioned previously, anthocyanins have been found to possess antioxidant/free radical scavenging properties that prevent oxidative stress, a phenomenon shown to negatively affect skin health and appearance.

The *Ugni molinae* leaf extract is preferably employed in an amount of from about 0.5 to about 3% by weight, and most preferably from about 1 to about 2% by weight, based on the total weight of the composition. This extract is commercially available from N-Active EIRL, under the trade name EthniCare® MURTA.

*Entada phaseoloides* bark/seed extract is derived from the seeds of a woody, evergreen vine from the Fabaceae family found in Africa, Asia, Australia, and the western Pacific. Its primary molecules include Entadamide A and Phaseoloidin. Entadamide A limits urocanic acid isomerization in skin, thereby inhibiting inflammation and immunosuppression, while also serving as a UV absorber. Phaseoloidin, a homogentisic acid glucoside, is a molecule with superior free-radical scavenging ability.

In a study entitled, "Experimental evaluation of anti-inflammatory effect of topical application of *Entada phaseoloides* seeds as paste and ointment," Dawane J, Pandit V, Rajopadhye B, *N Am J Med Sci*. 2011 November; 3(11): 513-517, the topical application of a paste and ointment containing the *Entada phaseoloides* bark/seed extract was confirmed as having potent anti-inflammatory properties.

The *Entada phaseoloides* bark/seed extract may be employed in an amount of from about 1 to about 5% by weight, and preferably in an amount of from about 2 to about 3% by weight, based on the total weight of the composition. This extract is commercially available from Biosil Technologies, Inc. headquartered in Allendale, N.J., under the trade name Entadine®.

The blend of the present disclosure comprises *Pfaffia paniculata, Ptychopetalum olacoides*, and *Lilium candidum* extracts. *Pfaffia paniculata* root extract is derived from a plant in the Amaranthaceae family typically found in South America. It is an extract characterized by the presence of vitamins, minerals, amino acids, phytosterols, pfaffic acid, pfaffosides, allantoin, mucilage, and saponins. This extract has been found to possess anti-inflammatory, immunostimulant, and analgesic properties.

*Ptychopetalum olacoides* bark/stem extract is derived from a flowering plant in the Olacaceae family indigenous to central Amazonian forests. The extract, which possesses antioxidant properties, is characterized by the presence of alkaloids, resinous materials rich in organic acids and tannins, traces of essential oils, sterols, triterpenic alcohols, and lupeol.

*Lilium candidum* extract is derived from the bulbs and flowers of the Liliaceae family. It is characterized by the presence of amino acids, flavonoids, glycosides, and steroids, and has been found to possess antifungal and anti-inflammatory properties. The blend of *Pfaffia paniculata, Ptychopetalum olacoides*, and *Lilium candidum* extracts is commercially available from Chemyunion LTDA, a Brazilian company headquartered in Sao Paulo, under the name Bioskinup™ Contour 3R.

The blend may be employed in embodiments of the disclosure in an amount of from about 1 to about 5% by weight, and preferably in an amount of from about 2 to about 3% by weight, based on the total weight of the composition.

The composition of the present disclosure further includes at least one humectant in order to further enhance the hydration and moisturization of the skin, thereby providing enhanced priming. The humectant will typically be employed in an amount of from about 1.0 to about 6.0% by weight, and preferably from about 1.5 to about 4.0% by weight, based on the total weight of the composition. Examples of suitable humectants include, but are not limited to, hyaluronic acid and its derivatives such as sodium hyaluronate and hydrolyzed hyaluronic acid, lecithin, aloe vera, panthenol, glycerin, and seaweed. A particularly preferred humectant for use in embodiments of the skin care compositions and methods of the present disclosure is hydrolyzed hyaluronic acid.

One of the key findings associated with compositions of the present disclosure is their ability to form a protective film on the surface of the skin. The inventors have surprisingly and unexpectedly discovered that certain combinations of natural polysaccharides, conventionally used to adjust a composition's viscosity (i.e., viscosity modifiers, a.k.a. rheology modifiers) and/or to impart a certain type of texture (i.e., texturizers), define a "film former" that facilitates the formation of an active ingredient-infused film which serves two unexpected yet important functions.

First, the unique active ingredient-infused film formed by the composition effectively inhibits airborne pollutants containing harmful particulate matter from contacting the skin.

Because the particulate matter itself contains harmful free radicals/ROS and/or it contains toxic chemicals that can drive free radical formation, either or both of which may result in oxidative stress to the skin's stratum corneum/skin barrier, inhibiting the particulate matter from contacting the skin in the first instance using the unique active ingredient-infused film formed by the composition reduces the likelihood of airborne pollutants inducing oxidative stress-related damage.

Secondly, it has been found that in addition to allowing the active ingredients present in the inventive compositions to be effectively infused within the film such that any free radicals/ROS associated with the particulate matter embedded in the film can be neutralized, the film also promotes penetration of active ingredients from the film into the stratum corneum, which neutralize free radicals/ROS present therein.

However, in order for the natural film former of the present disclosure (i.e., the disclosed combinations of polysaccharides) to facilitate formation of a film with these properties, the film former needs to possess a yield value that falls within a certain range. More particularly, the natural film former may have a yield value ranging from about 25 to about 100 Dynes/cm$^2$ measured at a shear rate of from about 0.1 to about 100 (s−1). Moreover, the film former also may remain stable in compositions having a pH below about 7, and preferably within a range of from about 4.5 to about 5.5.

In order to realize the required yield value and pH stability parameters, the film former oftentimes must be made from a mixture of two different natural polysaccharides. Examples of suitable polysaccharides which may be combined include, for example, but are not limited to, xanthan gum, carrageenan gum, konjac gum, sclerotium gum a.k.a. scleroglucan, starch, alginate, pectin, gum arabic, gellan gum, and the like. In one embodiment, the natural film former comprises a mixture of xanthan gum and sclerotium gum employed in amounts sufficient to create a natural film former in accordance with the present disclosure.

The film former will typically be employed in an amount of from about 0.1 to about 3.0% by weight, preferably from about 0.2 to about 2.0% by weight, and more preferably from about 0.5 to about 1.0% by weight, based on the total weight of the composition. A particularly preferred ingredient for use as a film former in the present disclosure is a product conventionally used to impart texture to a composition, the product commercially available from Cargill Corp. of Minneapolis, Minn. under the trade name Actigum™ VSX 20, comprising a combination of sclerotium gum and xanthan gum.

While film formers comprising a combination of naturally occurring, e.g., plant-derived, polysaccharides have been described, it will nevertheless be appreciated that the film former may be formed of one or more components that are not plant-derived, the components serving as a rheology modifier and/or texturizer and/or serving another purpose.

According to one embodiment of the present disclosure, there is provided a composition intended for application onto human skin suffering or at risk of suffering from oxidative stress, the composition comprising: (1) a mixture of at least: (a) from about 1 to about 10% by weight, and preferably from about 2% to about 5% by weight, of a leaf extract of *Aristotelia chilensis*; (b) from about 0.5 to about 3% by weight, and preferably from about 1 to about 2% by weight, of a leaf extract of *Buddleja globosa*; (c) from about 0.5 to about 3% by weight, and preferably from about 1 to about 2% by weight, of a leaf extract of *Ugni molinae*; (d) optionally, from about 1 to about 5% by weight, and preferably from about 2 to about 3% by weight, of a bark/seed extract of *Entada phaseoloides*; (e) optionally, from about 1 to about 5% by weight, and preferably from about 2 to about 3% by weight, of a blend of *Pfaffia paniculata, Ptychopetalum olacoides*, and *Lilium candidum* extracts; and (f) from about 1 to about 8% by weight, and preferably from about 2 to about 6% by weight, of at least one humectant, all weights based on the total weight of the composition; (2) an emulsifier; (3) a dermatologically acceptable carrier; and (4) a film former, wherein (a)-(f) are employed in amounts sufficient to neutralize existing free radicals present in the skin, while at the same time priming the skin by repairing and/or protecting the stratum corneum without unduly impairing its acid mantle, in order to enable the skin to protect itself against free-radical aggression caused by exposome-induced oxidative stress and dry skin-inducing water loss, thereby enhancing the skin's health and appearance, and wherein the composition is natural.

In another embodiment of the present disclosure, the inventors have surprisingly discovered that a natural preservative system comprising a combination of specific amounts of: a *Lactobacillus* ferment, a *Lactobacillus* and *Cocos nucifera* (coconut) fruit extract, salicylic acid (in some embodiments optional), a salt of a weak acid such as potassium sorbate, and propanediol which is optionally petroleum-free, when incorporated into a composition having a specific pH range, effectively both prohibits and inhibits microbial growth on and in the composition.

The *Lactobacillus* ferment of the present disclosure is preferably employed in an amount of from about 1 to about 5% by weight, preferably from about 2 to about 4% and more preferably from about 2 to about 4%, by weight of the total composition. A "*Lactobacillus* ferment" may refer to the solution obtained after fermentation of a defined growth medium by the bacterium *Lactobacillus* spp. During fermentation, *Lactobacillus* bacteria produce antimicrobial peptides that can provide broad-spectrum antimicrobial protection at appropriate concentrations and/or in combination with other antimicrobial agents. An exemplary *Lactobacillus* ferment is commercially available from Active Micro Technologies under the tradename Leucidal® SF.

The *Lactobacillus* and *Cocos nucifera* fruit extract can include any *Cocos nucifera* fruit extract fermented with *Lactobacillus* and/or included with *Lactobacillus* ferment of the present disclosure and is preferably employed in an amount of from about 1 to about 5%, preferably from about 2 to about 4%, by weight of the total composition. "*Cocos nucifera* fruit extract fermented with *Lactobacillus*," may reference the solution obtained after *Lactobacillus* fermentation of *Cocos nucifera* (coconut) fruit extract instead of a defined growth medium. The result is a materially different antimicrobial product that is effective at preventing the growth of fungi, specifically yeasts and molds, at appropriate concentrations and/or in combination with other antimicrobial agents. An exemplary *Lactobacillus* and *Cocos nucifera* extract is commercially available from Active Micro Technologies under the tradename Amticide® Coconut and is typically associated with the International Nomenclature of Cosmetic Ingredients (INCI) name of a *Lactobacillus* and *Cocos nucifera* (coconut) fruit extract.

When present, salicylic acid is preferably employed in an amount of up to about 0.5% by weight, preferably from about 0.1 to about 0.45% and more preferably from about 0.2 to about 0.4%, by weight of the total composition. It should be noted that the use of salicylic acid in an amount at or greater than about 0.5% by weight, based on the total weight of the composition, renders the composition a drug requiring FDA approval prior to commercialization and sale in the United States. In some embodiments, salicylic acid may be omitted by adjusting the concentrations of *Lactobacillus* ferment, *Lactobacillus* and *Cocos nucifera* fruit extract, and/or other ingredients as described in greater detail herein.

The salt of a weak acid is preferably employed in an amount of up to about 0.5% by weight, preferably from about 0.1 to about 0.45% and more preferably from about 0.2% to about 0.4%, by weight of the total composition. A preferred salt of a weak acid is potassium sorbate (i.e., the potassium salt of sorbic acid). Other weak acids that may be used in their salt form include, but are not limited to, acetic acid, propionic acid, and benzoic acid.

Propanediol, such as a petroleum-free 1,3-propanediol, is typically employed in an amount of about 1% to about 10% by weight, preferably from about 2% to about 8% and more preferably from about 4% to about 6%, by weight of the total composition. An exemplary petroleum-free 1,3-propanediol is commercially available from Dupont Tate & Lyle Bio Products under the tradename Zemea® Propanediol and can be associated with the INCI name propanediol.

The inventors have unexpectedly discovered that the ability of the preservative system of the present disclosure to effectively inhibit microorganism growth is critically dependent on the pH of the composition in which it is used. For example, if the preservative system is employed in a composition having a pH of 6, it fails to provide the requisite broad-spectrum protection needed for acceptable storage stability/shelf-life. Accordingly, the pH of a composition comprising the preservative system of the present disclosure may be in a range of from about 4.5 to about 5.5, and preferably from about 4.8 to about 5.3.

According to this embodiment of the present disclosure, there is provided a composition intended for application onto human skin in order to enhance its health and appearance, the composition comprising: (1) a preservative system that includes: (a) from about 1 to about 5%, preferably from about 2 to about 4% by weight, of a *Lactobacillus* ferment; (b) from about 1 to about 5%, preferably from about 2 to about 4% by weight, of a *Lactobacillus* and *Cocos nucifera* fruit extract; (c) up to about 0.5% by weight, preferably from about 0.1 to about 0.45, and most preferably from about 0.25 to about 0.4% by weight of salicylic acid; (d) from about 0.1 to about 0.5% by weight, and preferably from about 0.2 to about 0.4% by weight of at least one salt of a weak acid, preferably potassium sorbate; and (e) from about 1 to about 10%, preferably from about 2 to about 8% by weight, and most preferably from about 4 to about 6% by weight of 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides,* and *Lilium candidum* extracts; and (k) from about 1 to about 8% by weight, and preferably from about 2 to about 6% by weight, of at least one humectant, all weights based on the total weight of the composition; (3) an emulsifier; (4) a dermatologically acceptable carrier; and (5) a film former, wherein (f)-(k) are employed in amounts sufficient to neutralize existing free radicals present in the skin, while proactively priming the skin by repairing and/or protecting its stratum corneum without unduly impairing the stratum corneum's acid mantle, in order to enhance the skin's ability to defend itself against free-radical aggression caused by exposome-induced oxidative stress and dry skin-inducing water loss, thereby improving its health and appearance, and wherein the composition is natural, free of a skin-sensitizing amount of an essential oil, and has a pH ranging from about 4.5 to about 5.5, and preferably from about 4.8 to about 5.3.

In another embodiment of the present disclosure, there is provided a composition intended for application onto human skin in order to enhance its health and appearance, the composition comprising: (1) a preservative system that includes: (a) from about 1 to about 5%, preferably from about 2 to about 4% by weight, of a *Lactobacillus* ferment; (b) from about 1 to about 5%, preferably from about 2 to about 4% by weight of a *Cocos nucifera* fruit extract fermented with *Lactobacillus*; (c) from about 0.1 to about 0.45% by weight, preferably from about 0.25 to about 0.4% of salicylic acid; (d) up to about 0.5% by weight, preferably from about 0.2 to about 0.4% by weight, of at least one salt of a weak acid, preferably potassium sorbate; and (e) from about 1 to about 10%, preferably from about 2 to about 8% by weight, and most preferably from about 4 to about 6% by weight, of a petroleum-free propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides,* and *Lilium candidum* extracts; and (k) from about 1 to about 8% by weight, and preferably from about 2 to about 6% by weight, of at least one humectant, all weights based on the total weight of the composition; (3) an emulsifier; (4) a dermatologically acceptable carrier; and (5) a film former, wherein (f)-(k) are employed in amounts sufficient to neutralize existing free radicals present in the skin, while proactively priming the skin by repairing and/or protecting its stratum corneum's acid mantle, in order to enhance the skin's ability to defend itself against free-radical aggression caused by exposome-induced oxidative stress and dry skin-inducing water loss, thereby improving its health and appearance, and wherein the composition is natural, free of a skin-sensitizing amount of an essential oil, and has a pH ranging from about 4.5 to about 5.5, and preferably from about 4.8 to about 5.3.

According to yet another embodiment of the present disclosure, there is provided a composition intended for application onto human skin in order to enhance its health and appearance, the composition comprising: (1) a preservative system that includes: (a) from about 1 to about 5%, preferably from about 2 to about 4% by weight, of a *Lactobacillus* ferment; (b) from about 1 to about 5%, preferably from about 2 to about 4% by weight, of a *Cocos nucifera* fruit extract fermented with *Lactobacillus*; (c) from about 0.1 to about 0.45%, preferably from about 0.25 to about 0.4% by weight, of salicylic acid; (d) from about 0.1 to about 0.5% by weight, preferably from about 0.2 to about 0.4% by weight, of at least one salt of a weak acid, preferably potassium sorbate; and (e) from about 1 to about 10%, preferably from about 2 to about 8%, and most preferably from about 4 to about 6% by weight, of a petroleum-free 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; and (k) from about 1 to about 8% by weight, and preferably from about 2 to about 6% by weight, of at least one humectant, all weights based on the total weight of the composition; (3) an emulsifier; (4) a dermatologically acceptable carrier; and (5) a film former, wherein (f)-(k) are employed in amounts sufficient to neutralize existing free radicals present in the skin, while proactively priming the skin by repairing and/or protecting its stratum corneum without unduly impairing the stratum corneum's acid mantle, in order to enhance the skin's ability to defend itself against free-radical aggression caused by exposome-induced oxidative stress and dry skin-inducing water loss, thereby improving its health and appearance, and wherein the composition is natural, free of a skin-sensitizing amount of an essential oil, and has a pH ranging from about 4.5 to about 5.5, and preferably from about 4.8 to about 5.3.

In yet another embodiment of the present disclosure, there is provided a composition intended for application onto human skin in order to enhance its health and appearance, the composition comprising: (1) a preservative system comprised of: (a) from about 2 to about 4% by weight, of a *Lactobacillus* ferment; (b) from about 2 to about 4% by weight, of a *Cocos nucifera* fruit extract fermented with *Lactobacillus*; (c) from about 0.25 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; and (k) from about 1 to about 8% by weight, and preferably from about 2 to about 6% by weight, of at least one humectant, all weights based on the total weight of the composition; (3) an emulsifier; (4) a dermatologically acceptable carrier; and (5) a film former, wherein (f)-(k) are employed in amounts sufficient to neutralize existing free radicals present in the skin, while proactively priming the skin by repairing and/or protecting its stratum corneum without unduly impairing the stratum corneum's acid mantle, in order to enhance the skin's ability to defend itself against free-radical aggression caused by exposome-induced oxidative stress and dry skin-inducing water loss, thereby improving its health and appearance, and wherein the composition is natural, free of a skin-sensitizing amount of an essential oil, and has a pH ranging from about 4.5 to about 5.5, and preferably from about 4.8 to about 5.3.

According to another embodiment of the present disclosure, there is provided a composition intended for application onto human skin in order to enhance its health and appearance, the composition comprising: (1) a preservative system comprised of: (a) from about 2 to about 4% by weight, of a *Lactobacillus* ferment; (b) from about 2 to about 4% by weight, of a *Cocos nucifera* fruit extract fermented with *Lactobacillus*; (c) from about 0.25 to about 0.4% by weight, of salicylic acid; (d) from about 0.2 to about 0.4% by weight, of at least one salt of a weak acid, preferably potassium sorbate; and (e) from about 4 to about 6% by weight, of a petroleum-free 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; and (k) from about 1 to about 8% by weight, and preferably from about 2 to about 6% by weight, of at least one humectant, all weights based on the total weight of the composition; (3) an emulsifier; (4) a dermatologically acceptable carrier; and (5) a film former, wherein (f)-(k) are employed in amounts sufficient to neutralize existing free radicals present in the skin, while proactively priming the skin by repairing and/or protecting its stratum corneum without unduly impairing the stratum corneum's acid mantle, in order to enhance the skin's ability to defend itself against free-radical aggression caused by exposome-induced oxidative stress and dry skin-inducing water loss, thereby improving its health and appearance, and wherein the composition is natural, free of a skin-sensitizing amount of an essential oil, and has a pH ranging from about 4.5 to about 5.5, and preferably from about 4.8 to about 5.3.

According to another embodiment of the present disclosure, there is provided a composition intended for application onto human skin in order to enhance its health and appearance, the composition comprising: (1) a preservative system comprised of: (a) about 4% by weight, of a *Lactobacillus* ferment; (b) about 4% by weight, of a *Cocos nucifera* fruit extract fermented with *Lactobacillus*; (c) about 0.4% by weight, of potassium sorbate; and (e) about 4% by weight, of a petroleum-free 1,3-propanediol; (2) a mixture of at least: (f) from about 1 to about 10% by weight, and preferably from about 2 to about 5% by weight, of a leaf extract of *Aristotelia chilensis*; (g) from about 0.5 to about 3% by weight, and preferably from about 1 to about 2% by weight, of a leaf extract of *Buddleja globosa*; (h) from about 0.5 to about 3% by weight, and preferably from about 1 to about 2% by weight, of a leaf extract of *Ugni molinae*; (i) optionally, from about 1 to about 5% by weight, and preferably from about 2 to about 3% by weight, of a bark/seed extract of *Entada phaseoloides*; (j) optionally, from about 1 to about 5% by weight, and preferably from about 2 to about 3% by weight, of a blend of *Pfaffia paniculata, Ptychopetalum olacoides*, and *Lilium candidum* extracts; (k) from about 1 to about 8% by weight, and preferably from about 2 to about 6% by weight, of at least one humectant, all weights based on the total weight of the composition; (3) an emulsifier; (4) a dermatologically acceptable carrier; and (5) a film former, wherein (f)-(j) are employed in amounts sufficient to neutralize existing free radicals present in the skin, while proactively priming the skin by repairing and/or protecting its stratum corneum without unduly impairing the stratum corneum's acid mantle, in order to enhance the skin's ability to defend itself against free-radical aggression caused by exposome-induced oxidative stress and dry skin-inducing water loss, thereby improving its health and appearance, and wherein the composition is natural, free of a skin-sensitizing amount of an essential oil, and has a pH ranging from about 4.5 to about 5.5, and preferably from about 4.8 to about 5.3.

The dermatologically acceptable carrier can encompass a wide variety of forms. In some cases, the solubility or dispersibility of the components in the composition may dictate the form and character of the carrier. Non-limiting examples include simple solutions (e.g., aqueous or anhydrous), dispersions, emulsions, and solid forms. In certain embodiments, the dermatologically acceptable carrier is in the form of an emulsion. An emulsion can be generally classified as having a continuous aqueous phase (e.g., oil-in-water and water-in-oil-in-water) or a continuous oil phase (e.g., water-in-oil or oil-in-water). While the oil phase may comprise any vegetable oil, so long as it does not cause skin sensitization, a particularly preferred oil component is almond oil.

The inventors have surprisingly discovered that the use of almond oil enables compounds present in the botanical extract to effectively penetrate into the skin, without having to use skin-sensitizing essential oils, while still facilitating the desired degree of efficacy. This is due to almond oil being rich in beta-zoosterol, squalene, and alpha-tocopherol, together with lesser amounts of carbohydrates, proteins, vitamins, and minerals such as vitamin B complex (comprising vitamins B1, B2, B3, B5, B6, B7, B9, B12) and zinc. Moreover, almond oil's phytochemicals are believed to be effective at inducing surface level proliferation and skin cell development. Other oils that may also be used include, but are not limited to, vegetable oils such as olive oil, jojoba oil, babassu oil, castor oil, coconut oil, corn oil, cotton seed oil, linseed oil, mustard oil, safflower oil, sesame oil, soybean oil, sunflower seed oil, wheat germ oil, argan oil and manila oil.

Any ingredient capable of emulsifying the composition may be employed as an emulsifier without departing from the spirit of the disclosure, so long as it is natural and/or dermatologically acceptable. Examples thereof include, but are not limited to, glyceryl stearate, cetyl alcohol, sodium stearoyl lactylate, sorbitan olivate, cetearyl olivate, cetearyl alcohol, cetearyl glucoside, sodium cetearyl sulfate, and the like. It is also particularly preferred that the emulsifier be free of palm oil.

The compositions of the present disclosure may be made available to consumers in a wide variety of product forms that include, but are not limited to, solutions, suspensions, lotions, creams, gels, sprays, ointments, foams, and serums. For example, a product intended for application onto skin, post-shaving, in order to help relieve the irritation associated with the mechanical stress on the skin caused by the shaving process, can be formulated using the above-described compositions as a base formula.

In an embodiment, a product intended for application onto skin prior to or during exposure to sunlight, in order to serve as a sunscreen or sunblock, may be formulated according to the above-described compositions as a base formula.

According to embodiments of the present disclosure, the compositions can also additionally comprise suitable optional ingredients as desired. For example, the composition can optionally include other active or inactive ingredients, provided they do not unacceptably alter the benefits of the skincare composition, are natural, and/or do not promote skin sensitization. The precise amount of optional ingredients will be determined by those skilled in the art.

Examples of optional additive ingredients that may be employed include, but are not limited to, humectants, emollients, flavonoids, minerals, chelating agents, pH regulators/buffers, rheology modifiers, phytosterols, vitamin B3 compound, anti-inflammatory agents such as licorice extracts, bisabolol, manjistha extracted from plants in the genus *Rubia*, guggal extracted from plants in the genus *Commiphora, Quillaja saponaria* extract, kola extract, chamomile, red clover extract, sea whip extract, hibiscus extract, lucuma extract, ficus extract, red algae extract, sea kale extract, Iceland Moss extract, Saskatoon Berry extract, Siberian Ginseng extract, spruce needles extract, birch bark extract, yarrow extract, marigold extract, and couch grass extract.

Additional ingredients that may be employed in order to further potentiate the disclosure's efficacy may include, for example, *Peumus boldus* (Boldo) leaf extract, *Astrocaryum murumuru* seed butter, *Butyrospermum parkii* (shea) butter, *Theobroma grandiflorum* seed butter, *Spondias mombin* pulp extract, *Mangifera indica* pulp extract, *Musa sapientum* pulp extract, *Mauritia flexuosa* fruit oil, *Physalis angulata* extract, *Xylityl sesquicaprylate, Vaccinium myrtillus* seed oil, *Cucubita pepo* seed extract, linoleic acid, linolenic acid, *Centella asiatica* leaf extract, *Tamarindus indica* seed polysaccharide, *Zanthoxylum bungeanum* fruit extract, *Lactococcus* ferment lysate, *Bellis perennis* flower extract, *Coffea arabica* seed cake extract, *Coffea arabica* seed oil, cotton seed oil, linseed oil, *Pichia* ferment lysate filtrate, whey protein, mango, mombin plum, and dragon's blood.

A particularly preferred optional ingredient for use in the composition of the present disclosure is an emollient which may be employed in an amount of from about 1 to about 15% by weight, preferably from about 2 to about 5% by weight, and all weights therebetween. Examples of preferred emollients include, but are not limited to, seed butters such as *Astrocaryum murumuru* seed butter and *Theobroma grandiflorum* seed butter. These seed butters provide an enhanced degree of emollience to the compositions of the present disclosure. An especially preferred seed butter is *Astrocaryum murumuru* seed butter.

In addition to the above-mentioned ingredients, certain types of auxiliary ingredients may also be added to the composition of the present disclosure in order to prophylactically inhibit free-radical formation caused by UV radiation, which induces oxidative stress in the skin, in order to facilitate photoinhibition.

Examples of such auxiliary ingredients include, but are not limited to, *Pongamia glabra* (karanja) seed oil derived from the pongolote tree, *Dunaliella salina* algae extract which is rich in beta-carotene, *Haematococcus pluvialis* algae extract which is rich in astaxanthin, red algae which is rich in mycosporine-like amino acids, zinc oxide, and titanium dioxide.

The *Peumus boldus* (Boldo) leaf extract, when employed, will typically be used in an amount of from about 0.1 to about 5.0% by weight, such as from about 0.5 to about 3.0% by weight, and from about 1.0 to about 2.0% by weight, based on the weight of the composition.

In yet another embodiment of the present disclosure, there is provided a method of treating and/or priming skin suffering from oxidative stress or at risk of suffering from oxidative stress in order to enhance its health and/or appearance, by applying one of the above-disclosed compositions onto the skin.

A further embodiment of the present disclosure provides for a method of proactively priming and enhancing human skin's ability to defend itself against free radical aggression by applying one of the above-disclosed compositions onto the skin.

EXAMPLES

The following examples as set forth herein are intended for illustrative purposes only and are not intended to limit the scope of the disclosure in any way, as many variations thereof are possible without departing from the spirit and scope of the disclosure. In the examples, all concentrations are listed as weight percent, unless otherwise specified.

Example 1

A mixture of: *Aristotelia chilensis*+*Buddleja globosa*+*Ugni molinae* leaf extracts (hereinafter, "EthniCare® M3") was evaluated for total glutathione quantification and superoxide dismutase (SOD) activity, in a lysate cell via an enzymatic assay. The absorbance reading was performed at 410 nm for total glutathione and 450 nm for SOD using a Multiscan GO monochromator available from Thermo Fisher Scientific of Waltham, Mass. The quantification values were normalized by the total protein in the sample using the Bradford technique, as described in *Anal. Biochem,* 72:248-254.

Primary human fibroblasts were seeded in 75 $cm^2$ flasks, cultured, and expanded in an incubator at 37° C. in the presence of 5% $CO_2$. Upon reaching confluency, the cells were seeded in well plates and exposed to hydrogen peroxide and the quantification mediators.

For statistical evaluation, an ANOVA test was used to initially measure the variation in the results, after which a Bonferroni post-test was used to make the ANOVA results even more precise. A 5% significance level was used.

The bar graph 100 of FIG. 1 shows the amount of SOD activity in human fibroblasts exposed to varying amounts of EthniCare® M3 110, 112, 114, as compared to the oxidative stress group $H_2O_2$ 108 and a baseline control 106 ($P<0.001$).

Here, it is seen that EthniCare® M3 110, 112, 114 resulted in a significant increase in protective effect against oxidative stress, at various concentration levels, based on increased SOD activity, with a standard deviation of 3. Hence, whereas oxidative stress caused by exposing the human fibroblasts to $H_2O_2$ 108 resulted in a decrease of SOD activity, subsequent exposure by EthniCare® M3 increased SOD activity by approximately 100%.

With regards to total glutathione production in human fibroblasts, the bar graph 200 in FIG. 2 below further corroborates the protective effect obtained when using EthniCare® M3.

Here too it is seen that EthniCare® M3 results in a significant increase in human fibroblast protective effect against oxidative stress, at various concentration levels 210, 212, 214 of EthniCare® M3, based on increased total glutathione production, with the same standard deviation of 3. Hence, whereas oxidative stress to human fibroblasts caused by $H_2O_2$ 208 exposure resulted in a decrease of total glutathione, subsequent exposure to EthniCare® M3 210, 212, 214 significantly increased total glutathione production.

Figure 2:
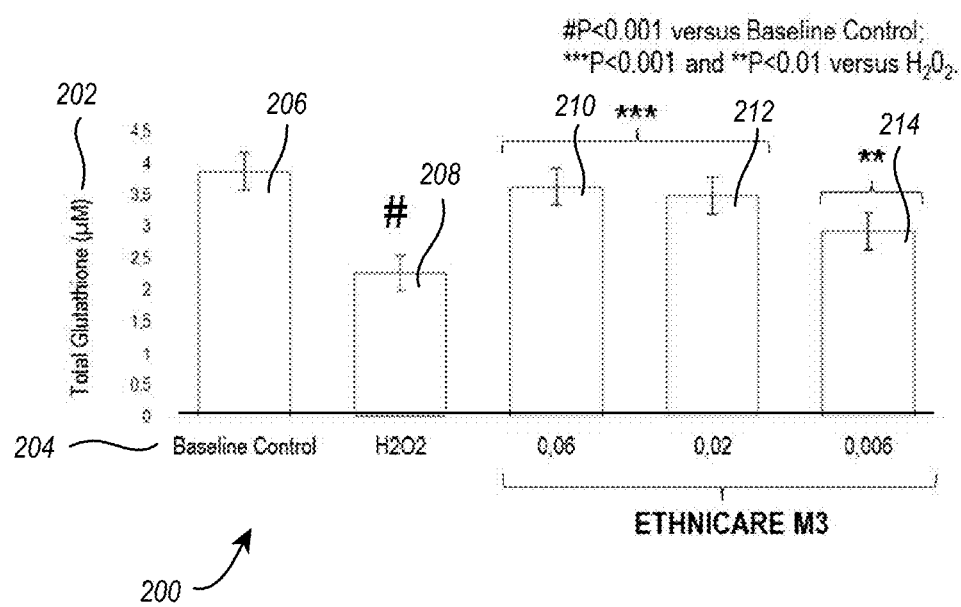
FIG. 2 illustrates levels of superoxide dismutase activity in response to different compositions including components of embodiments of the disclosure.

The results in FIGS. 1 and 2 demonstrate the significant antioxidant activity realized by EthniCare® M3, in view of its ability to strengthen cellular antioxidant capacity by modulating the antioxidant mediators SOD and total glutathione.

Example 2

In this example, the photo-protective effect of EthniCare® M3 against visible light ranging from 400-700 nm was evaluated, since long-term exposure to visible light has been shown to induce oxidative stress that can contribute to unwanted skin pigmentation (dark spots), inflammation, and oxidative photo-aging. Visible blue radiation (440-485 nm), also referred to as "blue light," has the ability to penetrate deeper into the skin than both UVA and UVB light, all the way to the dermis where collagen and elastin reside. Aside from the sun, electronic devices such as smartphones and computer screens emit blue light that most people are exposed to, in large quantities, on a daily basis. The potential negative photo-aging consequences such exposure can have on skin is troubling.

In order to assess its blocking ability, a thin film of EthniCare® M3 was applied onto a Helioplate HD6 substrate from HelioScreen Labs. Transmission spectra were then obtained using a UV 2450 Shimadzu spectrophotometer with an integration sphere (ISR-240A), available from Shimadzu Corporation of Kyoto, Japan. The spectral sweep range was 400-700 nm with measurements taken three times to ensure accuracy, the results of which are found in FIG. 3.

Figure 3:
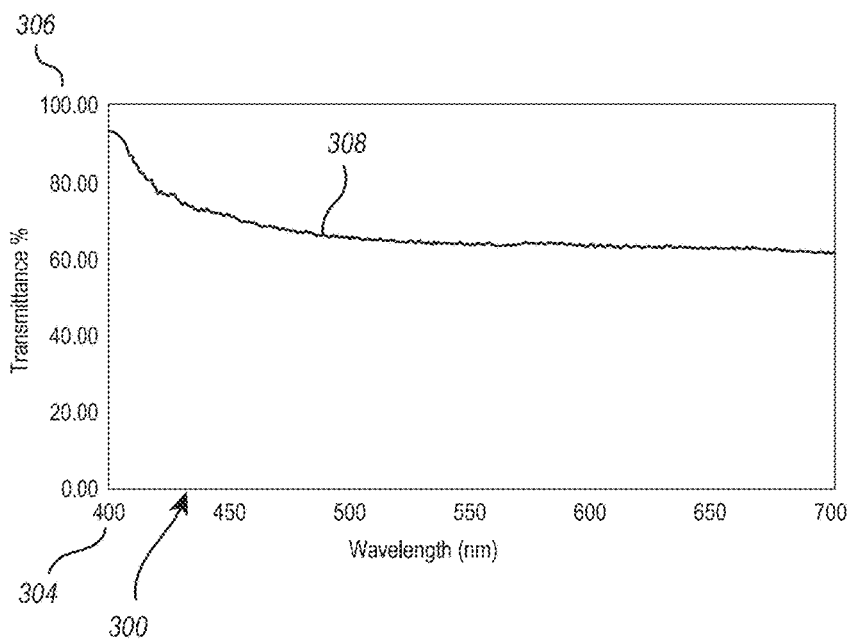
FIG. 3 illustrates transmissions spectra of components of embodiments of the disclosure.

As can be seen from the graph 300 of FIG. 3, the average transmittance 306 of blue light in the range of 440-485 nm, i.e., the UV range, is approximately 67%, with the mean being approximately 69%. Thus, approximately 31%, or one-third, of the blue light radiation was effectively blocked by EthniCare® M3, further evidencing its ability to inhibit oxidative stress and photo-aging damage.

Example 3

Leaf extracts *Aristotelia chilensis* and *Ugni molinae* were evaluated to determine their ability to prevent undesirable thymidine dimer formation upon exposure to UVB radiation. When skin is exposed to UVB radiation, thymidine bases in the DNA can absorb the UVB radiation to form thymidine dimers (also known as thymine dimers) in DNA, complicating the cell's efforts to replicate DNA and to properly function. In this experiment, an in-vitro thymidine dimer assay was performed using a skin model consisting of normal human-derived epidermal keratinocytes cultured to form a multilayered model of the human epidermis.

One group of tissue was treated for seven days with the *Aristotelia chilensis* leaf extract, another group of tissue was tested for seven days with the *Ugni molinae* leaf extract, and third group was left untreated. All three groups tissue groups were then exposed to UVB radiation at 300 $mJ/cm^2$. DNA was then extracted and assayed for thymidine dimer content.

The DNA was then immobilized and incubated with an antibody specific to thymidine dimers. The primary antibody was then detected with a secondary antibody conjugated to a fluorescent dye. The membrane was then scanned with an excitation laser and emission filter combo specific to the fluorescent dye, so that the fluorescence intensity of each sample was proportional to the amount of thymidine dimers present in the sample and a lower fluorescence intensity advantageously indicates lower levels of cellular damage from UVB radiation. The results of the thymidine dimer assay are found in Table 1, below, expressed as mean Relative Fluorescence Units (RFU)±standard deviation.

TABLE 1

|  | Corrected RFU |
|---|---|
| No UVB exposure | 514 ± 57.30 |
| Untreated | 5.463 ± 80.50 |
| 50 ug/ml Trolox (analog of vitamin E) | 4.380 ± 393.00 |
| *Aristotelia chilensis* at 5% | 3.418 ± 673.10 |
| *Ugni molinae* at 4% | 4.246 ± 426.30 |

The data in Table 1 shows that tissue treated with *Aristotelia chilensis* at 5% concentration resulted in a decrease of thymidine dimer formation of approximately 41%, and tissue treated with *Ugni molinae* at 4% concentration resulted in a decreased formation of thymidine dimer of approximately 25%, as compared to the untreated tissue, thus evidencing their photo-protective effect against UVB-induced DNA damage.

Example 4

In this example, EthniCare® M3 was evaluated to determine its effect on cutaneous erythema (i.e., sunburn). A total of 10 volunteers were recruited, each of which was subjected to mechanically induced erythema caused by the application and removal of transparent medical tape on their forearm for 20 successive repetitions. Erythema measurements were performed using a Mexameter® MX18 and Multiprobe Adapter MPA-5 available from Courage & Khazaka electronic GmbH, of Koln, Germany. An initial measurement was taken immediately after mechanical insult, followed by two additional measurements at intervals of 30 and 60 minutes. The results showed that all of the volunteers treated with EthniCare® M3 experienced a 41% reduction in erythema after 30 minutes, and a 76% reduction in erythema after 60 minutes, thereby evidencing the ability of EthniCare® M3 to soothe skin suffering from externally caused erythema.

These results show that the use of EthniCare® M3 provides a soothing action to skin suffering from erythema.

Example 5

In this example, EthniCare® M3 was evaluated to determine its effect on the production of nitric oxide in epidermal keratinocytes in culture. It is well known that the skin's exposure to external aggressors such as UV radiation, pollutants, chemical irritants, aesthetic treatments, and the like can often cause inflammatory reactions, resulting in erythema and edema, both of which are painful and unsightly. One of the factors that signals inflammation is nitric oxide (NO) produced endogenously by a variety of cells in order to regulate physiological processes such as neurotransmission, smooth muscle contractility, platelet reactivity, and cytotoxic activity of immune cells. High levels of NO have been found in pathologies such as rheumatoid arthritis and chronic intestinal inflammation, just to name a few.

Cultured epidermal keratinocytes (PAM 212 keratinocytes) were treated at three concentration levels of EthniCare® M3: 1%, 3%, and 5%. The cultured cells were first caused to express nitric oxide synthase leading to the production of NO from L-arginine. The control was a selective inhibitor of NO synthase, added to the cultured cells that completely (100%) inhibited NO production. NO production was measured using a colorimeter. The results obtained showed that: at 1% EthniCare® M3 inhibited 58.0% of NO production; at 3% it inhibited 46.2%; and at 5% it inhibited 25.3%, evidencing its effectiveness at alleviating skin inflammation.

Example 6

A composition in accordance with the present disclosure was evaluated to determine its ability to successfully pass a micro preservative efficacy testing (PET) challenge. The composition tested is found in Table 2 below.

TABLE 2

| Ingredient | Amount (wt %) |
|---|---|
| EthniCare ® M3 | 1.00 |
| *Lactobacillus* ferment | 4.00 |
| *Lactobacillus* and *Cocos nucifera* fruit extract ferment | 2.00 |
| Propanediol | 4.00 |
| Sodium benzoate | 0.30 |
| Potassium sorbate | 0.20 |
| Citric acid | 1.25 |
| Auxiliaries | 23.13 |
| Water | 64.12 |

Figure 4:
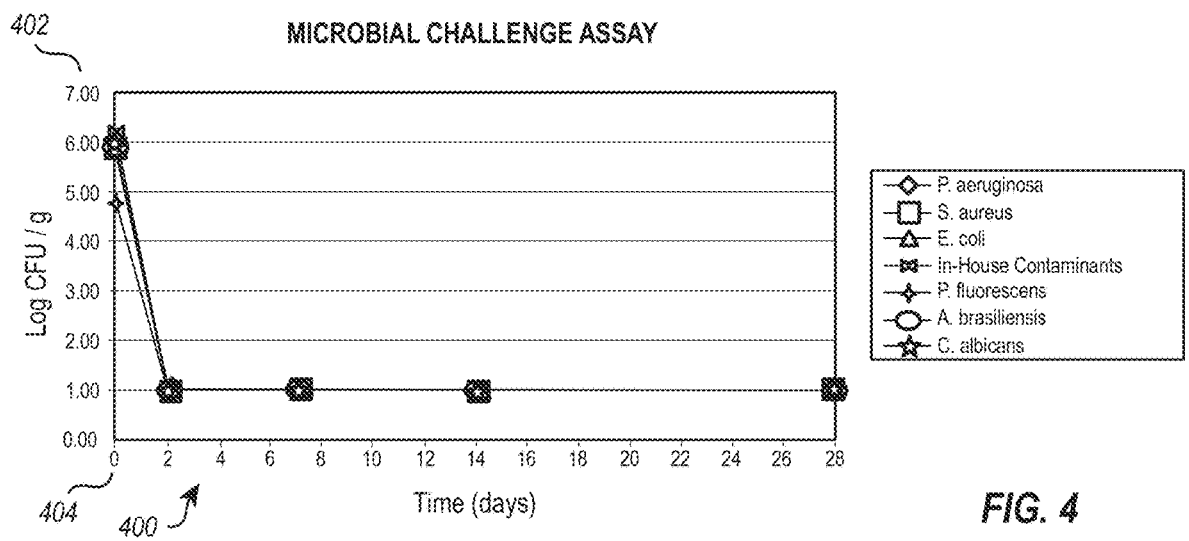
FIG. 4 illustrates the results of a microbial challenge assay using an exemplary all-natural preservative system in a composition according to an embodiment of the disclosure.

A graphical representation of the results of a microbial challenge assay performed for the exemplary skin care composition listed in Table 2 above is illustrated in FIG. 4. As seen in the graph 400 of FIG. 4, which shows the log of colony forming units (CFU)/g sample 402 as a function of days 404 after beginning the microbial challenge assay, the composition reduced each of *Pseudomonas aeruginosa*, *Staphylococcus aureus*, *Escherichia coli*, In-House Contaminants, *Pseudomonas fluorescens*, *Aspergillus brasiliensis*, and *Candida albicans* by day 2, with no subsequent uptick in any of the microbial species. The above test results confirm the successful preservation of the composition using the preservative system of the present disclosure in combination with EthniCare® M3.

Example 7

A composition in accordance with another embodiment the present disclosure was evaluated to determine its ability to successfully pass a micro PET challenge. The composition tested is found in Table 3 below.

TABLE 3

| Ingredient | Amount (wt %) |
|---|---|
| EthniCare ® M3 | 2.00 |
| Blend (*Pfaffia paniculata, Ptychopetalum olacoides,* and *Lilium candidum* extracts) | 2.00 |
| Propanediol | 4.00 |
| Essential oils | 0.44 |
| Glycerin | 2.00 |
| *Lactobacillus* ferment | 4.00 |
| *Lactobacillus* and *Cocos nucifera* fruit extract ferment | 2.00 |
| Propanediol | 4.00 |
| Sodium benzoate | 0.30 |
| Potassium sorbate | 0.20 |

TABLE 3-continued

| Ingredient | Amount (wt %) |
|---|---|
| Citric acid | 0.15 |
| Auxiliaries | 11.65 |
| Water | 71.26 |

Figure 5:
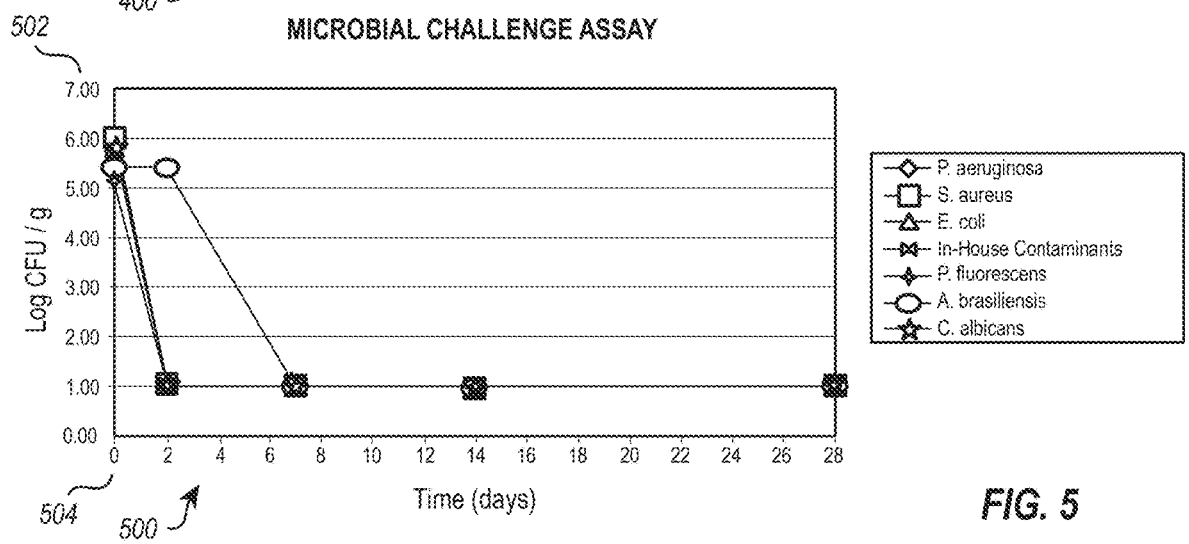
FIG. 5 illustrates the results of a microbial challenge assay using an exemplary all-natural preservative system in a composition according to another embodiment of the disclosure.

As seen in the graph 500 of FIG. 5, which shows the log CFU/g sample 502 as a function of days 504 after beginning the microbial challenge assay, the composition reduced each of *Pseudomonas aeruginosa, Staphylococcus aureus, Escherichia coli*, In-House Contaminants, *Pseudomonas fluorescens*, and *Candida albicans* by day 2, and *Aspergillus brasiliensis* by day 7, with no subsequent uptick in any of the microbial species. The above test results confirm the successful preservation of the composition using the preservative system of the present disclosure in combination with EthniCare® M3.

Example 8

A composition in accordance with the present disclosure was evaluated to determine its ability to successfully pass a micro (PET) challenge. The composition tested is found in Table 4 below.

TABLE 4

| Ingredient | Amount (wt %) |
|---|---|
| EthniCare ® M3 | 2.00 |
| Entadine ® | 2.00 |
| Propanediol | 4.00 |
| Essential oils | 0.34 |
| Glycerin | 2.00 |
| Emollient | 14.00 |
| *Lactobacillus* ferment | 4.00 |
| *Lactobacillus* and *Cocos nucifera* fruit extract ferment | 2.00 |
| Propanediol | 4.00 |
| Sodium benzoate | 0.30 |
| Potassium sorbate | 0.20 |
| Citric acid | 0.15 |
| Auxiliaries | 11.65 |
| Water | 71.26 |

Figure 6:
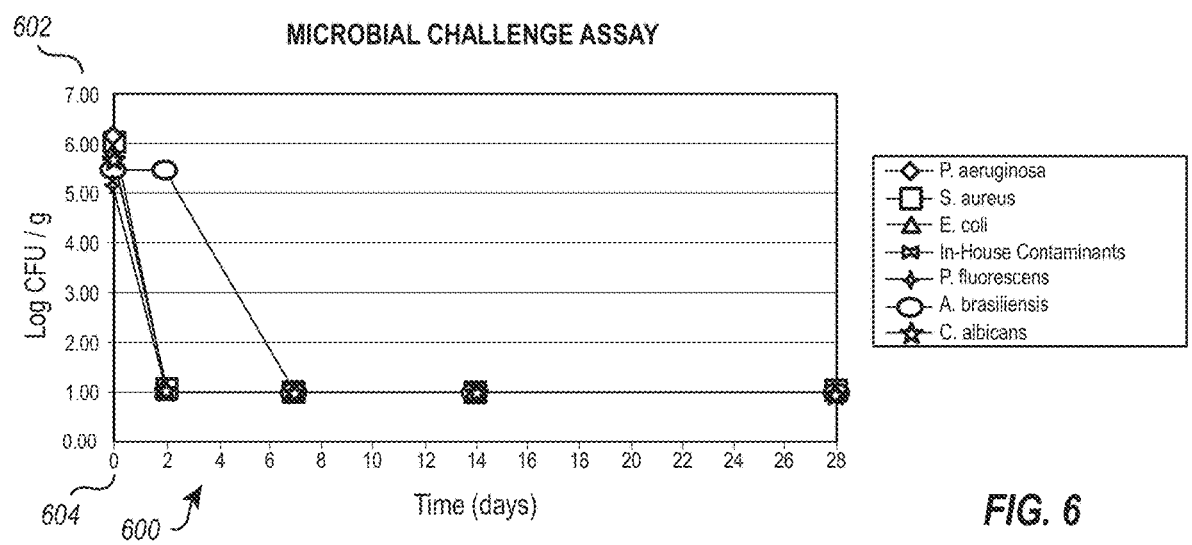
FIG. 6 illustrates the results of a microbial challenge assay using an exemplary all-natural preservative system in a composition according to another embodiment of the disclosure.

As seen in the graph 600 of FIG. 6, which shows the log CFU/g sample 602 as a function of days 604 after beginning the microbial challenge assay, the composition reduced each of *Pseudomonas aeruginosa, Staphylococcus aureus, Escherichia coli*, In-House Contaminants, *Pseudomonas fluorescens*, and *Candida albicans* by day 2, and *Aspergillus brasiliensis* by day 7, with no subsequent uptick in any of the microbial species. The above test results confirm the successful preservation of the composition using the preservative system of the present disclosure in combination with Ethnicare® M3, Entadine®, and/or other ingredients of a skin care composition for the treatment of oxidative stress according to the embodiments of the present disclosure.

Example 9

The ingredients *Peumus boldus* (Boldo) leaf extract, *Buddleja globosa* (Matico) leaf extract, *Aristotelia chilensis* (Maqui) leaf extract, and *Ugni molinae* (Murta) leaf extract were evaluated to determine what, if any, gene expression effects they may indicate after UVB exposure, per the below-indicated protocol.

Reconstructed Human Epidermis (RHE) tissues were obtained from ZenBio (Research Triangle Park, N.C.; lot #RHE051820) and were used immediately. Tissues were transferred to 6 well plates and were equilibrated for an hour in 1 ml of pre-warmed medium/well ZenSkin provided by the ZenBio. Samples of the above ingredients were then added non-diluted, in triplicates at 3 mg/cm$^2$ with the positive displacement pipette and were spread evenly on top of the RHE tissues. Sterile distilled water was the negative control. Tissues were allowed to incubate for a three-hour period with test materials, afterward were transferred to a new 24 well plate, and exposed to 30 mJ/cm$^2$ (equivalent to 1 minimal erythema dose, or MED) UVB (302 nm) using a Hoefer (Holliston, Mass.) transilluminator. Tissues were then placed back into the original six well plates with medium and allowed to incubate overnight.

At the end of the incubation RNA was extracted and purified with RNeasy Mini Kit cat. #74104 from Qiagen (Germantown, Md.), using a QiaCube Connect robotic station (Qiagen). Purified total RNA was assessed at 260 nm and 280 nm with a Thermo Fisher Scientific (Waltham, Mass.) NanoDrop™ Lite Spectrophotometer.

cDNA was prepared using a High-Capacity RNA-to-cDNA™ Kit (Applied Biosystems, Thermo Fisher) and the expression of the genes of interest was measured by real-time quantitative PCR with a BioRad iCycler iQ Detection System using PCR primers from Realtimeprimers (Elkins Park, Pa.) and AzuraView GreenFast qPCR Blue Mix LR available from Azura Genomics (Raynham, Mass.). Efficiency ΔΔCt method was used for quantification of results, after the normalization of gene expression to HPRT1 and GAPDH (housekeeping genes).

Genes were considered differentially expressed if the p value, as determined by the two-tailed t-test, was ≤0.10 and the modulation was ≥1.8.

Tissues treated with Boldo exhibited an anti-inflammatory (downregulation of CD44, MAP3K7, PTGS2, MMP1, IL8, ILIA; upregulation of TIMP2), anti-apoptotic (downregulation of FOXO3), anti-hyperproliferative (decrease of MAP3K7, PCNA, END1), vasculoprotective (upregulation of HSPG2, ITGB1), and barrier-protective (upregulation of AQP3, TGM1, LOR, downregulation of CD44) response. The decrease of UVB-induced proinflammatory signal by Boldo evidences a reduction in the need for antioxidant response (downregulation of TXNRD1 and perhaps CAT), with no apparent xenobiotic metabolism response.

Tissue treated with Matico decreased the expression of genes coding for late differentiation proteins (IVL, FLG, CDSN) and possibly increased cell survival (BIRC5), evidencing a potential photo-protective effect.

Tissue treated with Maqui showed Maqui to be a highly bioactive substance. It was found to support barrier-protection and ceramide production by way of its strong upregulation of AQP3 and LOR, as well as FLG and GBA, together with a decrease of HAS3 which is expected in differentiated layers of the epithelium and promoted by ascorbic acid, together with anti-inflammatory properties as evidenced by a significant decrease of IL-4, IL-6, and IL-8 activity.

Maqui was also found to trigger a decrease of the expression of AGER, which is the receptor for AGE (advanced glycation endproducts)—a major contributor to skin aging. Maqui also appeared to exhibit pigmentation-inducing effects through the inhibition of ASIP. Other modulated genes include VEGFA (stimulation of blood vessel growth and therefore skin oxygenation), TIMP (MMP inhibition), and TLR2 (upregulation), whose expression is important for repair of insults, such as those caused by UVB irradiation. Maqui-treated tissues also yielded significant amounts of RNA indicative of a broad photo-protective effect of that test material against UVB-induced cytotoxicity which is supported by the strong downregulation of the pro-apoptotic, UVB-induced FOXO3.

Tissue treated with Murta showed a complex bioactivity profile with pro-inflammatory effects (significant increase of IL1A, PTSG2, EDN1) combined with increased expression of genes coding for proteins important for stratum corneum formation (DSG3, TGM1, LOR) and skin repair after UVB irradiation (TLR2). Moreover, CTGF was significantly upregulated showing its potential for increasing ECM (extracellular matrix) production.

Tissue treated with the combination of Matico, Maqui, and Murta exhibited unusually robust bioactivity. Both the VEGFA and PPARD genes were upregulated, evidencing the biologic signaling initiated via the application of the combination of Matico, Maqui, and Murta. This type of immune system related cellular communication is the skin's biological response to environmental stressors. Environmental stressors related to UV radiation exposure can enable oxidative stress and attendant free radical formation on the skin. Similarly, both the IL8 and MT2A genes were down regulated evidencing the triggering of those biological processes of the skin associated with reducing inflammation caused by UV radiation exposure (i.e., anti-inflammatory effect). Lastly, the SMPD1, TGM1 and AQP3 genes were upregulated indicating that the combination triggered a biological process evidencing an enhancement of the skin's barrier function post-UV radiation exposure (i.e., skin priming function).

Example 10

A composition in accordance with the present disclosure was clinically tested to assess its ability to inhibit particulate matter from contacting the skin, i.e., its protective efficacy calculated as a percentage of skin protection (P %). The composition tested is found in Table 5 below.

TABLE 5

| Ingredients | % wt |
|---|---|
| Ethnicare ® M3 | 1.0 |
| Emollient | 15.5 |
| Humectant | 2.1 |
| *Lactobacillus* ferment | 4.0 |
| Coconut fermented and/or mixed with *Lactobacillus* | 2.0 |
| Potassium sorbate | 0.2 |
| 1,3-propanediol | 4.0 |
| Sodium benzoate | 0.3 |
| Emulsifier | 4.5 |
| Purified water | 59.3 |
| Additives | q.s. |
| Total | 100 |

Twenty-two individuals between the ages of 21-58 had 32 µL of the composition above applied evenly onto an area of one forearm (treated area) and nothing applied onto the same-sized area of their other forearm (non-treated area). Iron oxide particles having an average size of 1 µm, meant to mimic the size of particulate matter found in airborne pollutants, were then applied onto both the treated and non-treated areas using a make-up sponge. The particles were applied directly onto the area treated with the composition, whereas the untreated area was first moistened with water prior to the particles being applied thereon. A video-microscope fitted with a mobile fiber optic×20 lens, coupled with an image acquisition computer system was then used to measure the quantity of particles initially adhered onto both the treated and non-treated areas. Next, both the treated and non-treated areas were rinsed with water and then wiped with a dry cotton pad, after which a second measurement was taken to determine the quantity of particles removed from both areas of the skin.

The results showed that a significantly larger quantity of particles was captured by the treated area as compared to the non-treated area and that a significantly larger quantity of particles was rinsed from the treated versus non-treated area. These results yielded a percentage of protection value of +70% showing that the composition tested inhibited particles from contacting the skin.

Example 11

In this example, a composition in accordance with the present disclosure was clinically tested as in Example 10 to determine its ability to inhibit particulate matter from contacting the skin. The composition tested is found in Table 6 below.

TABLE 6

| Ingredients | % wt |
|---|---|
| Ethnicare ® M3 | 2.0 |
| Entadine ® | 2.0 |
| Emollient | 14.0 |
| Humectant | 2.1 |
| *Lactobacillus* ferment | 4.0 |
| Coconut fermented and/or mixed with *Lactobacillus* | 2.0 |
| Potassium sorbate | 0.2 |
| 1,3-propanediol | 4.0 |
| Sodium benzoate | 0.3 |
| Emulsifier | 7.4 |
| Purified water | 60.9 |
| Additives | q.s. |
| Total | 100 |

The results yielded a percentage of protection value of +92% showing that the composition tested inhibited particles from contacting the skin.

Example 12

In this example, a composition in accordance with the present disclosure was clinically tested as in Example 10 to determine its ability to inhibit particulate matter from contacting the skin. The composition tested is found in Table 7 below.

TABLE 7

| Ingredients | % wt |
|---|---|
| Ethnicare ® M3 | 2.0 |
| Bioskinup 3R | 3.0 |
| Emollient | 7.0 |
| Humectant | 2.1 |
| *Lactobacillus* ferment | 4.0 |
| Coconut fermented and/or mixed with *Lactobacillus* | 2.0 |
| Potassium sorbate | 0.2 |
| 1,3-propanediol | 4.0 |

TABLE 7-continued

| Ingredients | % wt |
| --- | --- |
| Sodium benzoate | 0.3 |
| Emulsifier | 2.0 |
| Purified water | 68.1 |
| Additives | q.s. |
| Total | 100 |

The results yielded a percentage of protection value of +88% showing that the composition tested inhibited particles from contacting the skin.

Example 13

In this example, a composition in accordance with the present disclosure was clinically tested as in Example 10 to determine its ability to inhibit particulate matter from contacting the skin. The composition tested is found in Table 8 below.

TABLE 8

| Ingredients | % wt |
| --- | --- |
| Ethnicare ® M3 | 2.0 |
| Bioskinup ® 3R | 2.0 |
| Emollient | 5.5 |
| Humectant | 2.0 |
| *Lactobacillus* ferment | 4.0 |
| Coconut fermented and/or mixed with *Lactobacillus* | 2.0 |
| Potassium sorbate | 0.2 |
| 1,3-propanediol | 4.0 |
| Sodium benzoate | 0.3 |
| Emulsifier | 2.0 |
| Purified water | 71.3 |
| Additives | q.s. |
| Total | 100 |

The results yielded a percentage of protection value of +92%, showing that the composition tested inhibited particles from contacting the skin.

Example 14

In this example, a composition in accordance with the present disclosure was clinically tested to assess the ability of its key active ingredients, infused within the film formed by the film former of the composition, to penetrate into the stratum corneum where the key active ingredients can be absorbed by the skin in order to neutralize free radicals/ROS present therein. The composition tested is found in Table 9 below.

TABLE 9

| Ingredients | % wt |
| --- | --- |
| Ethnicare ® M3 | 2.0 |
| Entadine ® | 2.0 |
| Emollient | 14.0 |
| Humectant | 2.1 |
| *Lactobacillus* ferment | 4.0 |
| Coconut fermented and/or mixed with *Lactobacillus* | 2.0 |
| Potassium sorbate | 0.2 |
| 1,3-propanediol | 4.0 |

TABLE 9-continued

| Ingredients | % wt |
| --- | --- |
| Sodium benzoate | 0.3 |
| Emulsifier | 7.4 |
| Purified water | 60.9 |
| Additives | q.s. |
| Total | 100 |

Two different analytical methods were used to ascertain active-ingredient penetration. Attenuated total reflection Fourier-transform infrared spectroscopy ("ATR-FTIR") imaging spectroscopy was performed to assess penetration within the stratum corneum, and Confocal Raman spectroscopy was performed to assess penetration beyond the stratum corneum into the epidermis. Samples of flash-frozen human skin, all from the same donor, were purchased from a licensed supplier and prepared for testing by being cut into 2.5 cm×2.5 cm pieces, thawed, and cleaned. In particular, the skin samples were then cleaned by twice tape-stripping each sample.

The cleaned samples were then imaged by ATR-FTIR to establish control images. 40 mg of the tested composition were then massaged onto the skin samples using a glass rod and allowed to sit for five minutes. The skin samples were then placed on a Franz diffusion cell for four hours at 32° C. After four hours, any excess product on the skin sample surfaces was gently blotted with a kimwipe. The samples were then imaged to evaluate initial product deposition on the skin surface.

Next, to determine penetration of the key active ingredients into the stratum corneum, eight tape strips were sequentially applied and removed from the surfaces of the skin samples. Six different layers of the stratum corneum were accessed via this tape stripping method: the surface of the stratum corneum and five layers beneath the surface. These measurements were taken after tape strips 1, 2, 4, 6, and 8, respectively. In order to evaluate and visualize the penetration of the composition's key active ingredients within the skin sample, ATR-FTIR imaging spectroscopy was used to scan the skin sample surfaces before and after sequential tape stripping.

The images were recorded on a Spotlight System 400 available from PerkinElmer of Waltham, Mass. with the use of an ATR-FTIR imaging accessory. The spectral resolution was set at 4 $cm^{-1}$, spatial resolution was set at 6.25 μm, the scan accumulation was 4, and the spectral range was 4000-750 $cm^{-1}$. All of the ATR-FTIR images were concatenated and baseline corrected. Untreated human skin was compared to skin treated with the composition of Table 9. The experiments were performed in triplicate. Further, two skin areas were investigated at each layer inside the stratum corneum.

Figure 7:
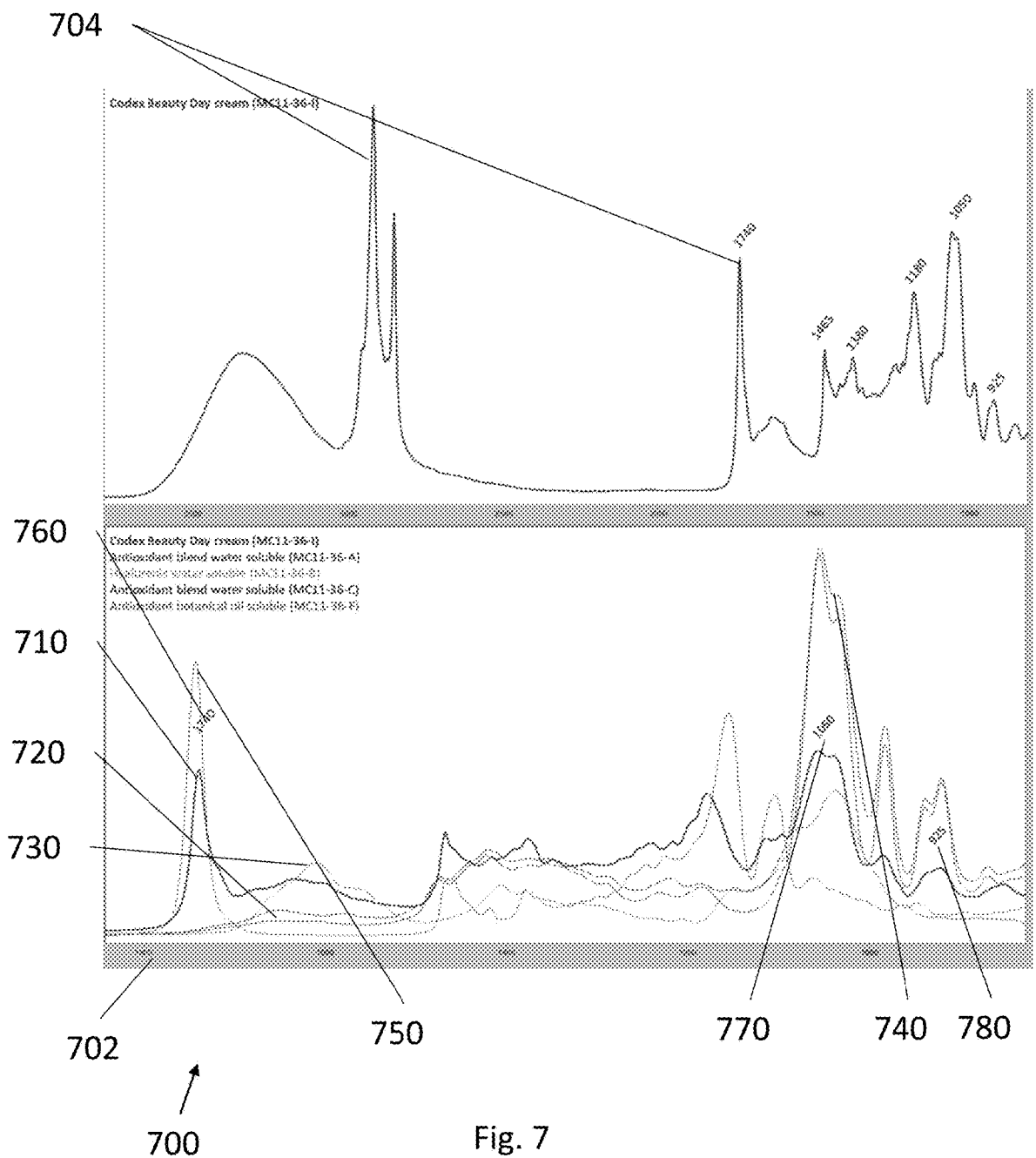
FIG. 7 illustrates the results of ATR-FTIR spectroscopy performed on skin samples treated with a skin care composition according to an embodiment of the disclosure.

Turning to FIG. 7, FTIR spectra of the tested composition and components thereof are shown in a graph 700. The FTIR spectra 704 in the graph 700 extend along a spectral range 702, for example from 4000-750 $cm^{-1}$. As seen, FTIR spectra corresponding to the composition 710 and to ingredients of the composition such as water-soluble antioxidant blends 720, 740, botanical oil-soluble antioxidant blend 750, and water-soluble hyaluronic blend 730.

Three IR markers were used to investigate the penetration of the composition of Table 9, particularly at bands 760, 770, 780 around 1740, 1050, and 925 $cm^{-1}$, respectively. It has been found that there is almost no overlap in this area with the skin contribution. That is, the IR band 760 around 1740 $cm^{-1}$ is mainly attributed to the botanical oil-soluble antioxidant blend 750, while the bands 770, 780 around 1050 and 925 cm$^{-1}$, respectively, are mainly attributed to the water-soluble antioxidant blends 720, 740.

Figure 8:
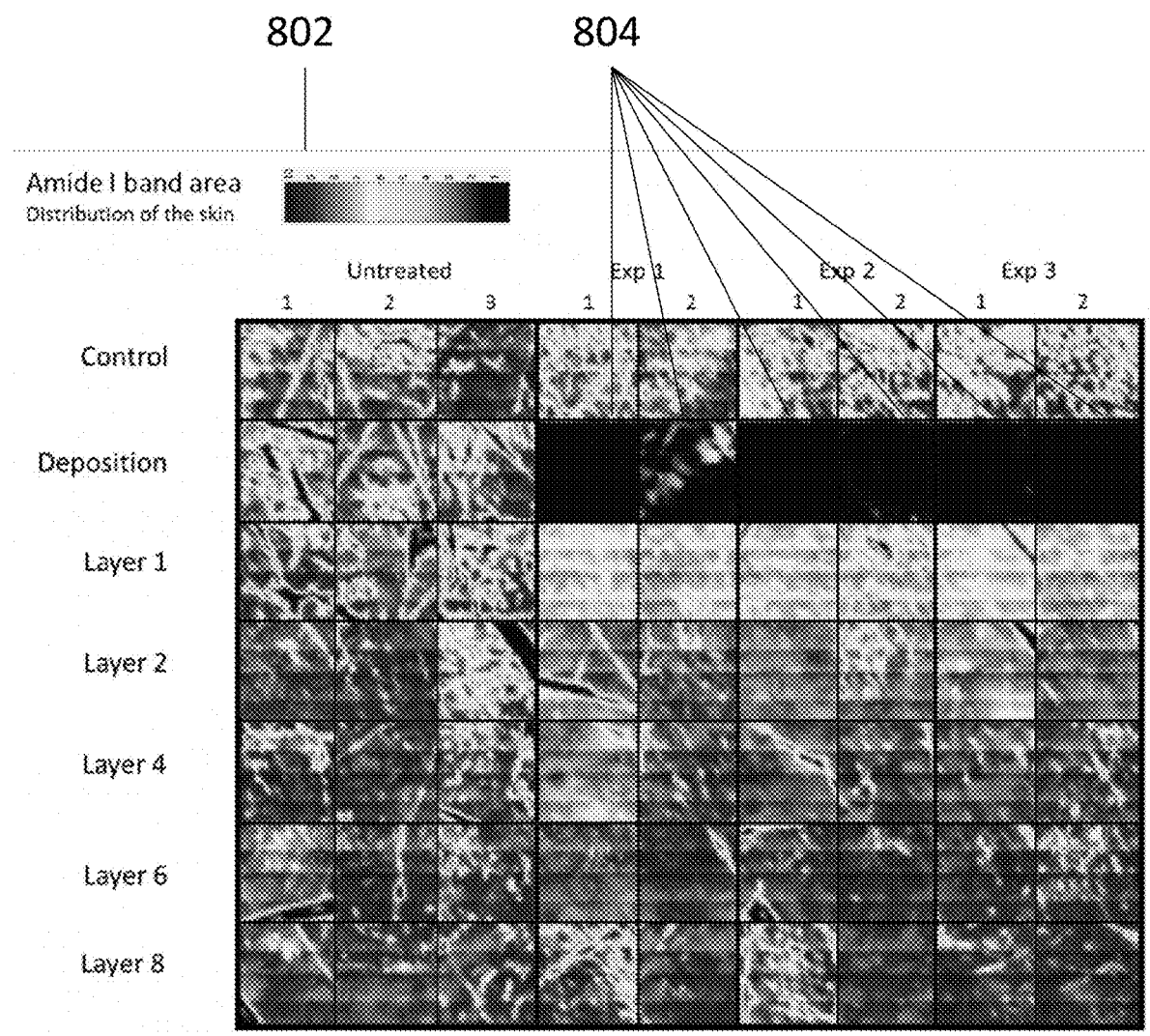
FIG. 8 illustrates the results of ATR-FTIR spectroscopy along the Amide I band area and performed on skin samples including a control group of untreated skin samples and skin samples treated with a skin care composition according to the embodiment of FIG. 7.

Turning now to FIG. 8, ATR-FTIR data 800 showing the distribution of the protein content on untreated human skin samples, defining a control group Untreated 1, 2, 3 after topical application of the composition and after sequential tape strips for triplicated samples Exp 1 1, 2, Exp 2 1, 2, and Exp 3 1, 2 are shown. Specific AFR-FTIR images were generated to visualize the skin distribution at different layers, i.e. control, deposition, Layer 1, Layer 2, Layer 4, Layer 6, and Layer 8. The data 800 show the Amide I band intensity 802, which is specific to the protein content of the skin. A higher protein content corresponds to a higher value.

The data 800 demonstrate that the protein content was uniform in all the human skin samples, and that only the ATR-FTIR images recorded four hours after topical application, i.e., deposition 804 of the composition on the skin surface presented a lower protein content indicated by a lower value of the Amide I band area 802, as a significant amount of the composition was present at the skin surface after the four-hour treatment time.

Figure 9:
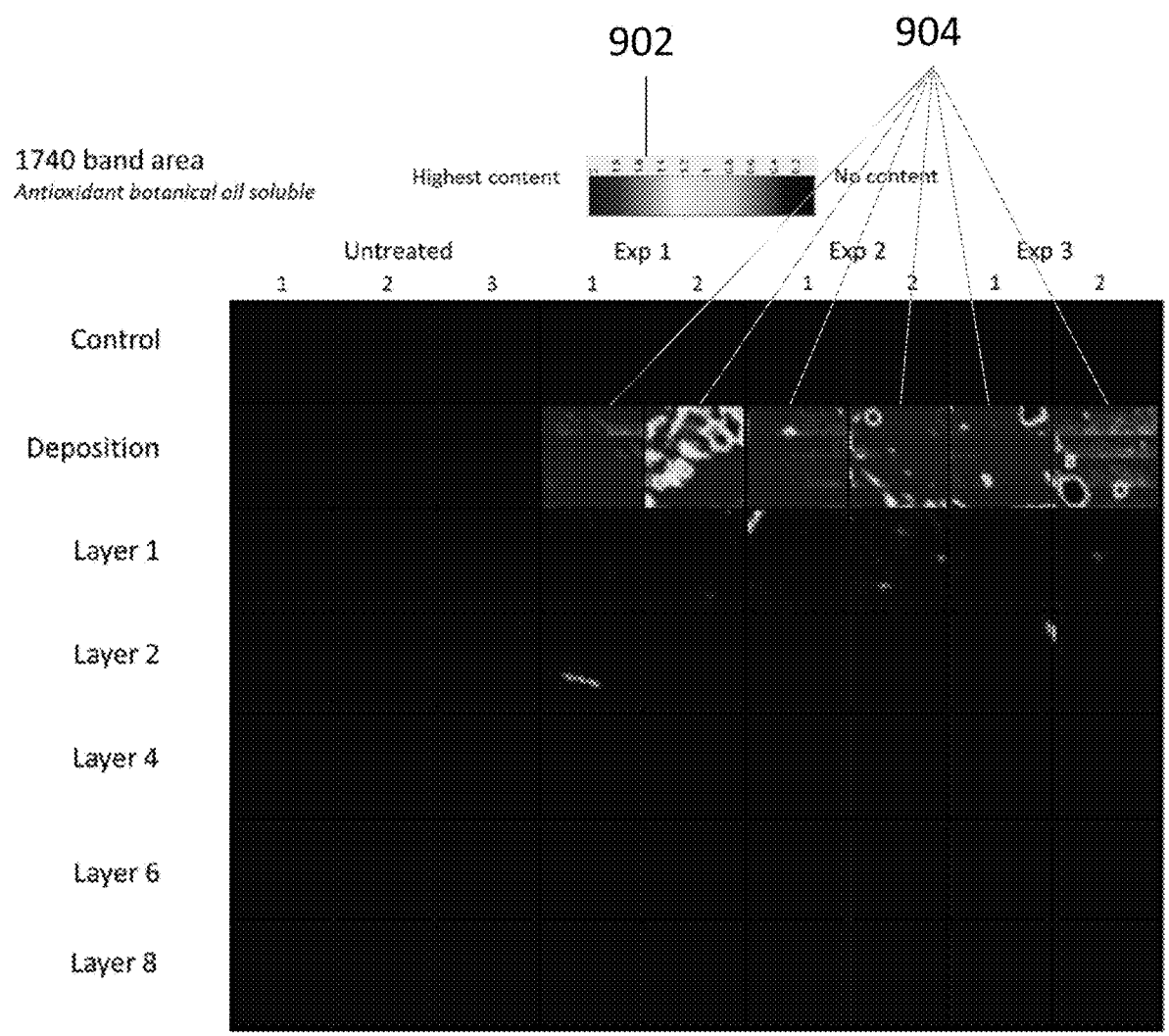
FIG. 9 illustrates the results of ATR-FTIR spectroscopy along the 1740 $cm^{-1}$ band area and performed on skin samples including a control group of untreated skin samples and skin samples treated with a skin care composition according to the embodiment of FIG. 7.

Turning now to FIG. 9, to visualize the distribution of the composition inside the stratum corneum, specific ATR-FTIR images were generated at the 1740 cm$^{-1}$ band area, the 1740 cm$^{-1}$ band area being specific to the composition, particularly the botanical oil-soluble antioxidant blend component thereof. The data 900 show the 1740 band area 902, which is specific to the botanical oil-soluble antioxidant blend component of the composition, and a higher value corresponds to a higher botanical oil-soluble antioxidant content. As seen in the ATR-FTIR images recorded four hours after topical application and treatment in the Franz cell, the composition was strongly detected at the surface, i.e., the deposition layer 904 of the human skin samples Exp 1 1, 2, Exp 2 1, 2, and Exp 31, 2.

By contrast, no penetration of the skin surface was detected in the untreated human skin samples Untreated 1, 2, 3 at any level after four hours of treatment in the Franz cell. Accordingly it has been surprisingly determined that the composition at this band area 902 did not penetrate into the stratum corneum, and no contribution was detected beyond the Layer 1. Thus it has been surprisingly determined that the botanical oil-soluble antioxidant component of the composition does not penetrate the stratum corneum after four hours of Franz cell treatment.

That is, while the oily lipid portion of the composition would be expected to penetrate below the surface of the skin in view of the affinity of the lipids for lipids present within the skin, it remains instead at the skin surface, demonstrating the properties of the film formed by the composition. As a result, particulate matter from airborne pollutants that are tripped by the film can then be neutralized by the botanical oil-soluble antioxidant diffused within the film.

Figure 10:
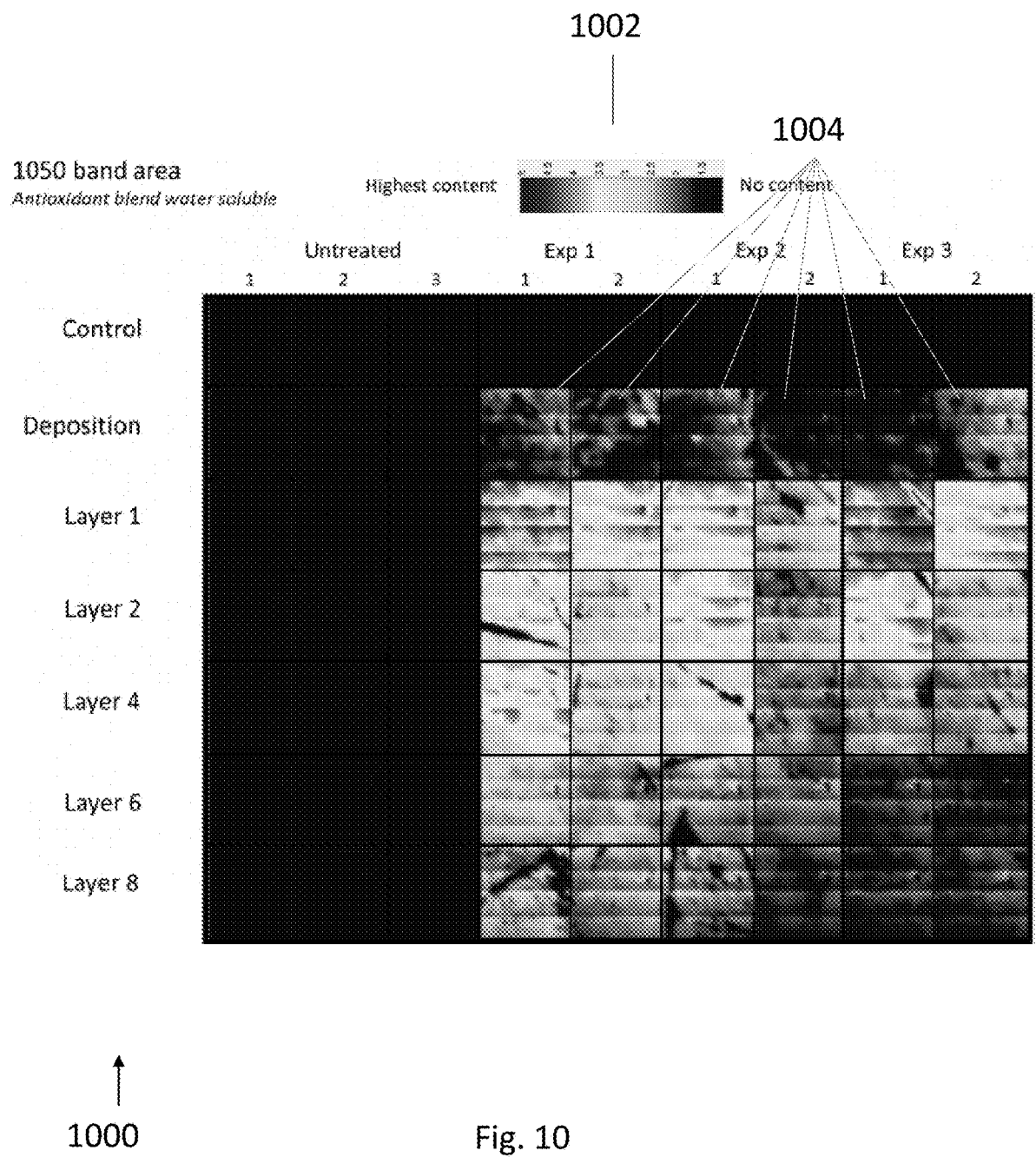
FIG. 10 illustrates the results of ATR-FTIR spectroscopy along the 1050 $cm^{-1}$ band area and performed on skin samples including a control group of untreated skin samples and skin samples treated with a skin care composition according to the embodiment of FIG. 7.

Turning now to FIG. 10, to visualize the distribution of the composition inside the stratum corneum, specific ATR-FTIR images were generated at the 1050 cm$^{-1}$ band area, the 1050 cm$^{-1}$ band area being specific to the water-soluble antioxidant blend component of the composition. The data 1000 show the 1050 band area 1002, which is specific to the water-soluble antioxidant blend component of the composition, and a higher value corresponds to a higher water-soluble antioxidant content. As observed previously, no penetration was detected in the untreated skin samples, i.e., the control group Untreated 1, 2, 3 at any layer of the skin. By contrast to the control group and to the findings regarding the 1740 cm$^{-1}$ band area, after a four-hour treatment in the Franz cell, the composition was slightly detected at the surface 1004 of the skin samples Exp 1 1, 2, Exp 2 1, 2, and Exp 3 1, 2. Based on the 1050 cm$^{-1}$ band marker, the composition penetrated deep inside the stratum corneum, from the deposition to the Layer 8. As the 1050 cm$^{-1}$ band marker corresponds to the water-soluble antioxidant blend, it has been found that the water-soluble components of the composition penetrate deep into the stratum corneum after a four-hour Franz cell treatment.

Figure 11:
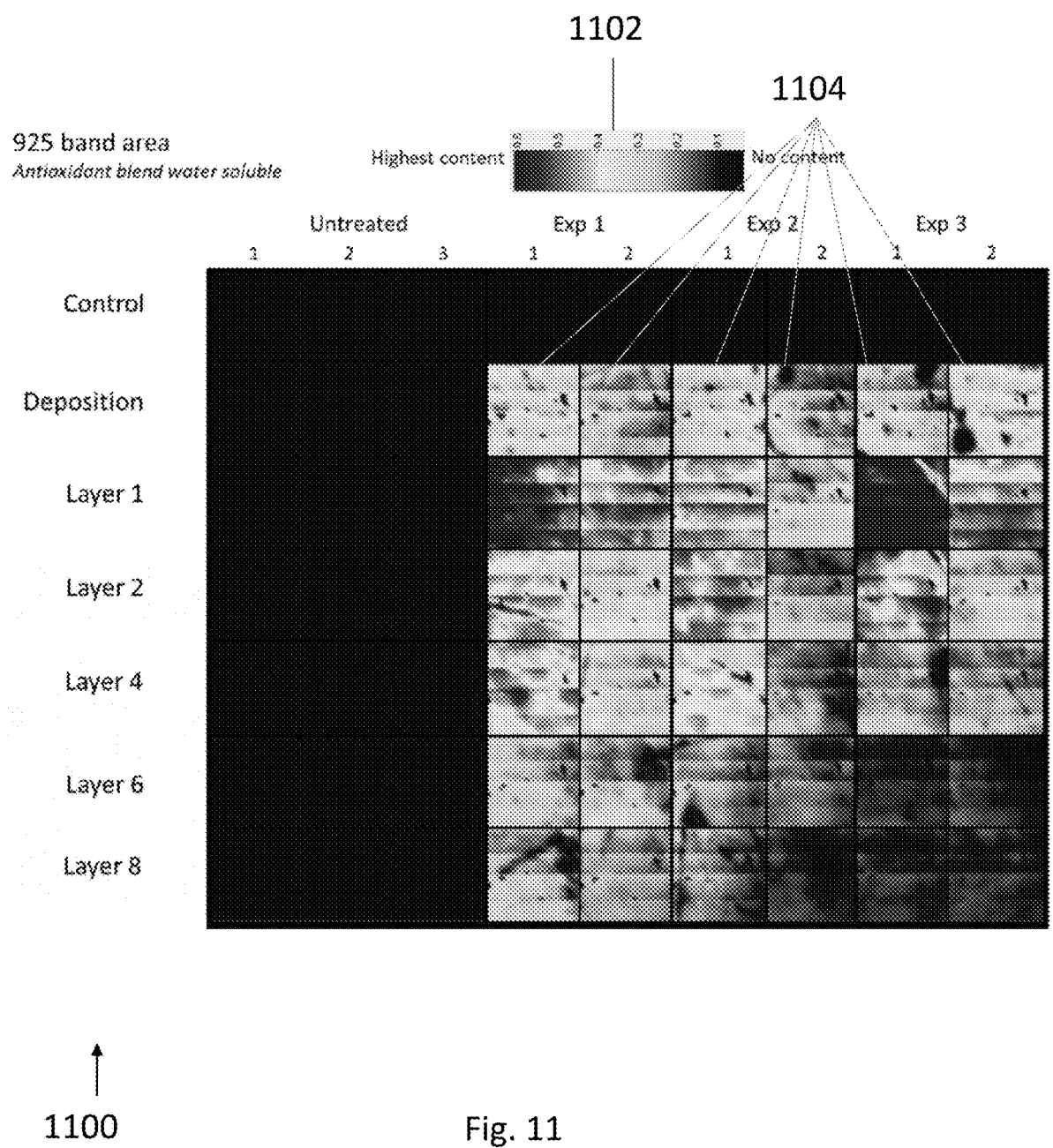
FIG. 11 illustrates the results of ATR-FTIR spectroscopy along the 925 $cm^{-1}$ band area and performed on skin samples including a control group of untreated skin samples and skin samples treated with a skin care composition according to the embodiment of FIG. 7.

Turning now to FIG. 11, specific ATR-FTIR images also were generated at the 925 cm$^{-1}$ band area, the 925 cm$^{-1}$ band area also being specific to the water-soluble antioxidant blend component of the composition. The data 1100 show the 925 band area 1102, which is specific to the water-soluble antioxidant blend component of the composition, and a higher value corresponds to a higher water-soluble antioxidant content. As observed previously, no penetration was detected in the untreated skin samples, i.e., the control group Untreated 1, 2, 3 at any layer of the skin.

By contrast to the control group and to the findings regarding the 1740 cm$^{-1}$ band area, after a four-hour treatment in the Franz cell, the composition was slightly detected at the surface 1104 of the skin samples Exp 1 1, 2, Exp 2 1, 2, and Exp 3 1, 2, validating the findings regarding the 1050 cm$^{-1}$ band area. Based on the 925 cm$^{-1}$ band marker, the composition penetrated deep inside the stratum corneum, from the deposition to the Layer 8. As the 925 cm$^{-1}$ band marker corresponds to the water-soluble antioxidant blend, it has been found that the water-soluble components of the composition penetrate deep into the stratum corneum after a four-hour Franz cell treatment. The antioxidants are available to scavenge and neutralize free radicals/ROS present within the stratum corneum due to their extension and penetration thereinto.

The data obtained from ATR-FTIR surprisingly show the ability of components of the composition of Table 9 to penetrate deep inside the stratum corneum, with different penetration depths for water-soluble antioxidants compared to botanical oil-soluble antioxidants.

Confocal Raman spectroscopy was also performed on skin samples to evaluate the composition. Spectra were recorded using a Confocal Raman Microscope such as the WITec Alpha-300 R Confocal Raman Microscope available from WITec GmbH of Ulm, Germany. The Alpha-300 R is a single spectrum microscope and configured for line scans and large area scans and comprises images stacks. The spectra were collected with spectral resolution of 4 cm$^{-1}$, spectral range of 4000-400 cm$^{-1}$, laser excitation of 532 nm, laser power of 20 mw, and laser exposure of 20 seconds.

Figure 12:
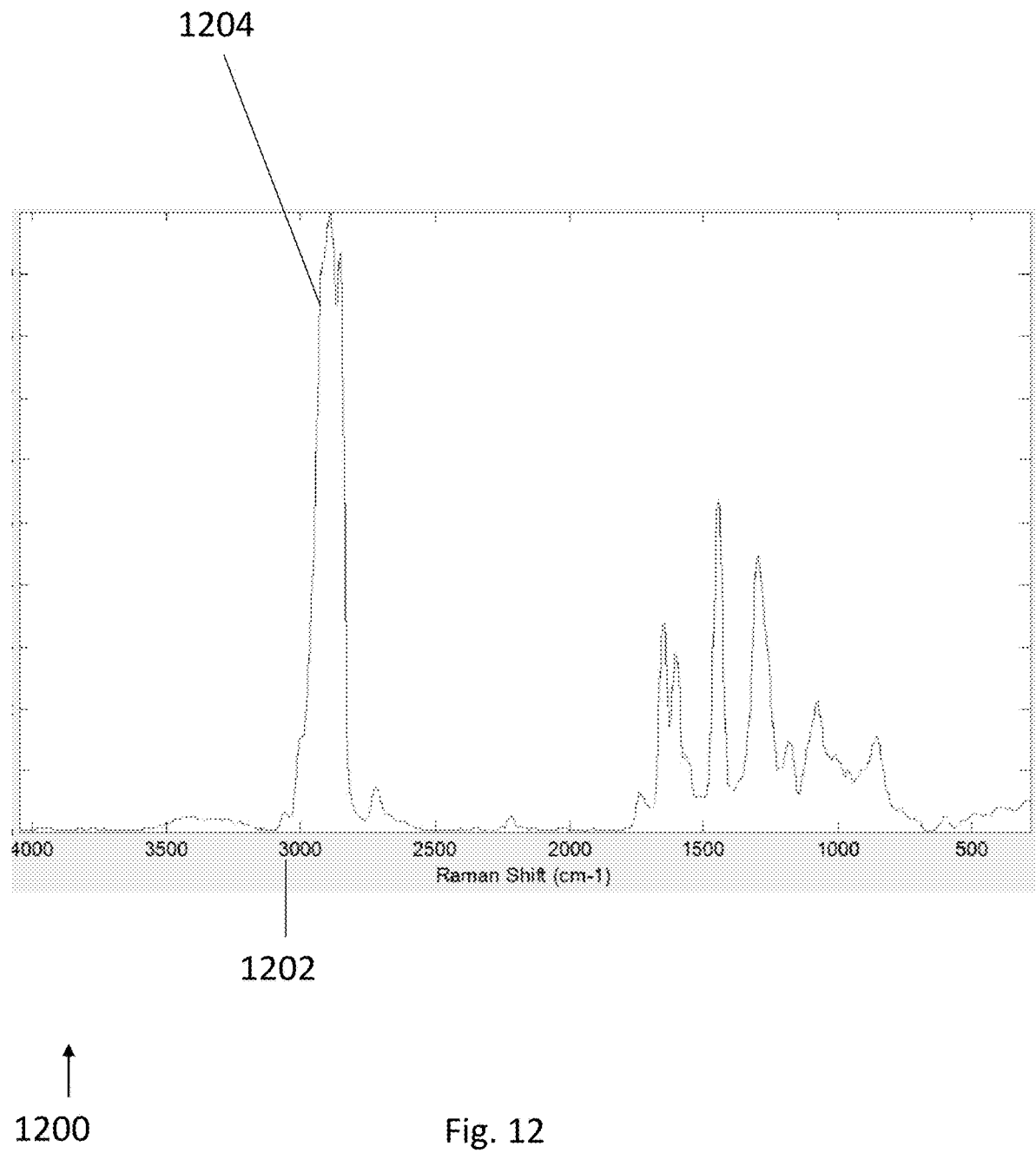
FIG. 12 illustrates the results of Confocal Raman spectroscopy performed on a skin sample treated with a skin care composition according to the embodiment of FIG. 7.

As seen in FIG. 12, a graph 1200 shows a spectrum 1204 along a spectral range 1202. The spectrum 1204 corresponds to the composition of Table 9 above. Confocal Raman images for the composition show the coefficient of correlation based on the spectrum 1204 for the composition. Values for the coefficient of correlation are between 0 and 1, with 1 representing the highest correlation and 0 the lowest. The Confocal Raman images were generated using false color, with the highest values given in brighter colors and the lowest in darker colors. The coefficient of correlation, 0.7, on untreated skin is used as the baseline that corresponds to no composition in the skin samples. Thus the scale 1304 of FIG. 13 ranges from 0.7 to 1.0.

Figure 13:
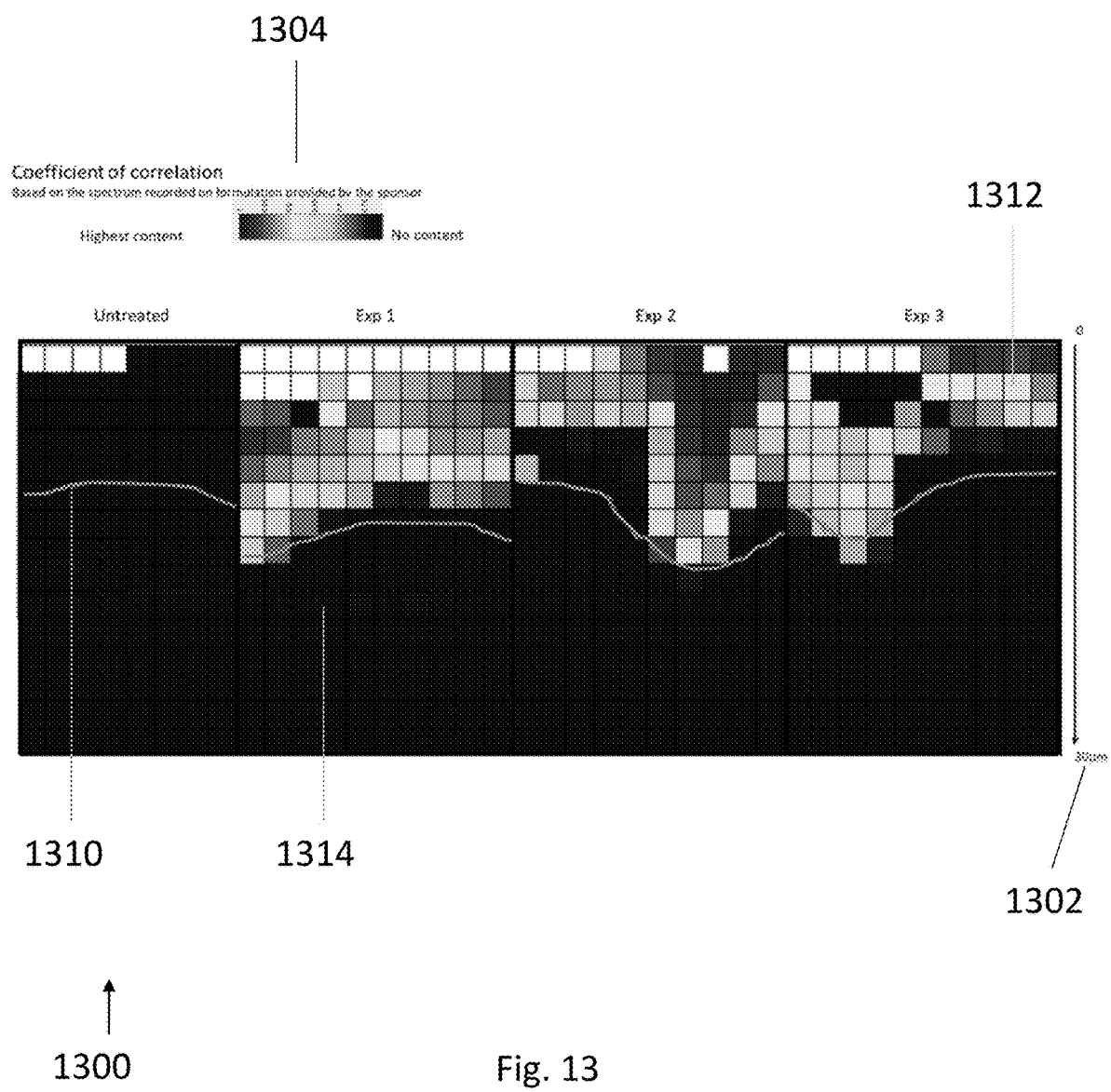
FIG. 13 illustrates the results of Confocal Raman spectroscopy performed on skin samples including a control group of untreated skin samples and skin samples treated with a skin care composition according to the embodiment of FIG. 7.

As seen in FIG. 13, Confocal Raman data 1300 corresponding to untreated skin and triplicated treated skin Exp 1, Exp 2, Exp 3 are shown along a depth from 0 to 30 µm, 0 corresponding to the skin surface and 30 µm corresponding to a depth from the skin surface. A line 1310 denotes the location of the boundary between stratum corneum 1312 and the epidermis 1314. Similar to the observations from the ATR-FTIR spectroscopy data described and depicted regarding FIGS. 7-11, there was no detection of the composition at any depth in the control group, i.e., the untreated skin samples. By contrast, after a four-hour treatment time in the Franz cell, the composition was detected in the first 8-14 µm below the skin surface. Surprisingly it was found that the composition was detected through the entire stratum corneum 1312 but not in or beyond the epidermis 1314.

The above-referenced examples establish the efficacy of the disclosed embodiments to enhance skin suffering from oxidative stress caused by external stressors such as UV radiation and environment pollution, as well as to prime the skin in order to enhance and protect its barrier function capability, thereby allowing it to better defend itself against external aggressors, including oxidative stress-inducing airborne particulate matter. The embodiments may advantageously comprise one or a combination of a *Peumus boldus* (Boldo) leaf extract, *Buddleja globosa* (Matico) leaf extract, *Aristotelia chilensis* (Maqui) leaf extract, and *Ugni molinae* (Murta) leaf extract, which may synergistically enhance, prime, and/or relieve the skin.

By providing a skin care composition and methods according to the present disclosure, the problem of existing skin care compositions and methods intended for treatment and prevention of oxidative stress comprising non-natural ingredients, harsh synthetic preservatives, and other harmful components is addressed. The embodiments of the present disclosure advantageously provide a composition effective for neutralizing free radicals in the skin and/or priming the skin for in order to enhance its ability to defend itself against free-radical aggression.

The skin care composition and method embodiments address the problem of existing skin care treatment modalities being non-natural and/or being inadequate for treating skin conditions such as oxidative stress. Additionally, by providing a skin care composition and method according to the embodiments, a film may be advantageously formed on a user's skin, the film serving to trap particulate matter and to provide antioxidants that can neutralize the particulate matter before damage is done to the skin.

What is claimed is:

1. A composition for application onto human skin, the composition comprising:
    (1) a mixture of at least:
        (a) about 1 to about 10% by weight of a leaf extract of *Aristotelia chilensis*;
        (b) about 0.5 to about 3% by weight of a leaf extract of *Buddleja globosa*;
        (c) about 0.5 to about 3% by weight of a leaf extract of *Ugni molinae*;
        (d) optionally, about 1 to about 5% by weight of a bark/seed extract of *Entada phaseoloides*;
        (e) optionally, about 1 to about 5% by weight of a blend of *Pfaffia paniculata, Ptychopetalum olacoides*, and *Lilium candidum* extracts; and
        (f) about 1.0 to about 8.0% by weight of at least one humectant;
    (2) an emulsifier;
    (3) a dermatologically acceptable carrier; and
    (4) a film former;
        wherein (a)-(f) synergistically neutralize existing free radicals present in the skin, while proactively priming the skin in order to enhance the skin's ability to defend itself against free radical aggression caused by exposome-induced oxidative stress and dry skin-inducing water loss, thereby improving its health and appearance;
        wherein the composition is natural, free of a skin-sensitizing amount of an essential oil, and has a pH ranging from about 4.5 to about 5.5, and
        wherein the composition is in the form of a solution, suspension, lotion, cream, gel, spray, ointment, foam, serum, or combination thereof.

2. The composition of claim 1, wherein (a) is employed in an amount of from about 1 to about 10% by weight; (b) is employed in an amount of from about 0.5 to about 3% by weight; (c) is employed in an amount of from about 0.5 to about 3% by weight; (d) is employed in an amount of from about 1 to about 5% by weight, when present; and (f) is employed in an amount of from about 1.0 to about 6.0% by weight, all weights based on the total weight of the composition.

3. The composition of claim 1, wherein (a) is employed in an amount of from about 1 to about 10% by weight; (b) is employed in an amount of from about 0.5 to about 3% by weight; (c) is employed in an amount of from about 0.5 to about 3% by weight; (e) is employed in an amount of from about 1 to about 5% by weight, when present; and (f) is employed in an amount of from about 1.0 to about 6.0% by weight, all weights based on the total weight of the composition.

4. The composition of claim 1, wherein the film former has a yield value of from about 25 to about 100 Dynes/cm$^2$.

5. The composition of claim 1, wherein the film former is employed in an amount of from about 0.2 to about 2.0% by weight, based on the total weight of the composition.

6. The composition of claim 1, wherein (a) is employed in an amount of from about 2 to about 5% by weight; (b) is employed in an amount of from about 1 to about 2% by weight; (c) is employed in an amount of from about 1 to about 2% by weight; (d) is employed in an amount of from about 2 to about 3% by weight, when present; (e) is employed in an amount of from about 2 to about 3% by weight, when present; and (f) is employed in an amount of from about 1.5 to about 4.0% by weight, all weights based on the total weight of the composition.

7. The composition of claim 1, wherein (a) is employed in an amount of from about 2 to about 5% by weight; (b) is employed in an amount of from about 1 to about 2% by weight; (c) is employed in an amount of from about 1 to about 2% by weight; (d) is employed in an amount of from about 2 to about 3% by weight, when present; (e) is employed in an amount of from about 2 to about 3% by weight, when present; and (f) is employed in an amount of from about 2.0 to about 6.0% by weight, all weights based on the total weight of the composition.

8. A composition for application onto human skin, the composition comprising:
    (1) a preservative system comprising:
        (a) from about 1 to about 5% by weight of a *Lactobacillus* ferment;
        (b) from about 1 to about 5% by weight, of a *Lactobacillus* and *Cocos nucifera* fruit extract;
        (c) up to about 0.5% by weight of salicylic acid;
        (d) from about 0.1 to about 0.5% by weight of at least one salt of a weak acid; and
        (e) from about 1 to about 10% by weight of a petroleum-free 1,3-propanediol;
    (2) a mixture of at least:
        (f) about 1 to about 10% by weight of a leaf extract of *Aristotelia chilensis*;

(g) about 0.5 to about 3% by weight of a leaf extract of *Buddleja globosa*;
(h) about 0.5 to about 3% by weight of a leaf extract of *Ugni molinae*;
(i) optionally, about 1 to about 5% by weight of a bark/seed extract of *Entada phaseoloides*;
(j) optionally, about 1 to about 5% by weight of a blend of *Pfaffia paniculata, Ptychopetalum olacoides*, and *Lilium candidum* extracts; and
(k) about 1.0 to about 8.0% by weight of at least one humectant,
wherein (f)-(k) synergistically neutralize existing free radicals present in the skin, while proactively priming the skin in order to enhance its ability to defend itself against free radical aggression caused by exposome-induced oxidative stress and dry skin-inducing water loss;
(3) an emulsifier;
(4) a dermatologically acceptable carrier; and
(5) a film former;
wherein the composition is natural, free of a skin sensitizing-effective amount of an essential oil, and has a pH ranging from about 4.5 to about 5.5.

9. The composition of claim 8, wherein (a) is employed in an amount of from about 2 to about 4% by weight; (b) is employed in an amount of from about 2 to about 4% by weight; (c) is employed in an amount of from about 0.1 to about 0.45% by weight; and (d) is employed in an amount of from about 0.2 to about 0.4% by weight; and (e) is employed in an amount of from about 2 to about 8% by weight, all weights based on the total weight of the composition.

10. The composition of claim 8, wherein (f) is employed in an amount of from about 1 to about 10% by weight; (g) is employed in an amount of from about 0.5 to about 3% by weight; (h) is employed in an amount of from about 0.5 to about 3% by weight; (i) is employed in an amount of from about 1 to about 5% by weight, when present; (j) is employed in an amount of from about 1 to about 5% by weight, when present; and (k) is employed in an amount of from about 1.0 to about 6.0% by weight, all weights based on the total weight of the composition.

11. The composition of claim 8, wherein (f) is employed in an amount of from about 2 to about 5% by weight; (g) is employed in an amount of from about 1 to about 2% by weight; (h) is employed in an amount of from about 1 to about 2% by weight; (i) is employed in an amount of from about 2 to about 3% by weight, when present; (j) is employed in an amount of from about 2 to about 3% by weight, when present; and (k) is employed in an amount of from about 1.5 to about 4.0% by weight, all weights based on the total weight of the composition.

12. The composition of claim 8, wherein (f) is employed in an amount of from about 2 to about 5% by weight; (g) is employed in an amount of from about 1 to about 2% by weight; (h) is employed in an amount of from about 1 to about 2% by weight; (i) is employed in an amount of from about 2 to about 3% by weight, when present; (j) is employed in an amount of from about 2 to about 3% by weight, when present and (k) is employed in an amount of from about 2.0 to about 6.0% by weight, all weights based on the total weight of the composition.

13. The composition of claim 8 wherein the film former has a yield value of from about 25 to about 100 Dynes/cm$^2$.

14. The composition of claim 8 wherein the film former is employed in an amount of from about 0.2 to about 2.0% by weight, based on the total weight of the composition.

15. A method of simultaneously treating skin and proactively priming the skin in order to enhance its ability to defend itself against free radical aggression by applying onto the skin a composition comprising:
(1) a mixture of at least:
(a) about 1 to about 10% by weight of a leaf extract of *Aristotelia chilensis*;
(b) about 0.5 to about 3% by weight of a leaf extract of *Buddleja globosa*;
(c) about 0.5 to about 3% by weight of a leaf extract of *Ugni molinae*;
(d) optionally, about 1 to about 5% by weight of a bark/seed extract of *Entada phaseoloides*;
(e) optionally, about 1 to about 5% by weight of a blend of *Pfaffia paniculata, Ptychopetalum olacoides*, and *Lilium candidum extracts*; and
(f) about 1.0 to about 8.0% by weight of at least one humectant;
(2) an emulsifier;
(3) a dermatologically acceptable carrier, and
(4) a film former,
wherein (a)-(f) synergistically neutralize existing free radicals present in the skin, while proactively priming the skin in order to enhance its ability to defend itself against free radical aggression caused by exposome-induced oxidative stress and dry skin-inducing water loss, thereby improving its health and appearance; and
wherein the composition is natural, free of a skin sensitizing-effective amount of an essential oil, and has a pH of from about 4.5 to about 5.5.

16. The method of claim 15, wherein (a) is employed in an amount of from about 1 to about 10% by weight; (b) is employed in an amount of from about 0.5 to about 3% by weight; (c) is employed in an amount of from about 0.5 to about 3% by weight; (d) is employed in an amount of from about 1 to about 5% by weight, when present; (e) is employed in an amount of from about 1 to about 5% by weight, when present; and (f) is employed in an amount of from about 1.0 to about 6.0% by weight, all weights based on the total weight of the composition.

17. The method of claim 15, wherein the film former has a yield value of from about 25 to about 100 Dynes/cm$^2$.

18. The method of claim 15, wherein the film former is employed in an amount of from about 0.2 to about 2.0% by weight, based on the total weight of the composition.

19. The method of claim 15, wherein (a) is employed in an amount of from about 2 to about 5% by weight; (b) is employed in an amount of from about 1 to about 2% by weight; (d) is employed in an amount of from about 1 to about 2% by weight; (d) is employed in an amount of from about 2 to about 3% by weight, when present; (e) is employed in an amount of from about 2 to about 3% by weight, when present; and (f) is employed in an amount of from about 1.5 to about 4.0% by weight, all weights based on the total weight of the composition.

20. The composition of claim 15, wherein (a) is employed in an amount of from about 2 to about 5% by weight; (b) is employed in an amount of from about 1 to about 2% by weight; (c) is employed in an amount of from about 1 to about 2% by weight; (d) is employed in an amount of from about 2 to about 3% by weight, when present; (e) is employed in an amount of from about 2 to about 3% by weight, when present; and (f) is employed in an amount of from about 2.0 to about 6.0% by weight, all weights based on the total weight of the composition.

* * * * *